(12) United States Patent
Candas et al.

(10) Patent No.: US 7,183,100 B2
(45) Date of Patent: Feb. 27, 2007

(54) ACONITASE

(75) Inventors: Mehmet Candas, Dallas, TX (US); Lee A. Bulla, Tioga, TX (US)

(73) Assignee: Biological Targets, Inc., Tioga, TX (US)

( * ) Notice: Subject to any disclaimer, the term of this patent is extended or adjusted under 35 U.S.C. 154(b) by 424 days.

(21) Appl. No.: 10/441,919

(22) Filed: May 19, 2003

(65) Prior Publication Data

US 2004/0248276 A1 Dec. 9, 2004

Related U.S. Application Data

(60) Provisional application No. 60/459,885, filed on Apr. 1, 2003, now abandoned.

(51) Int. Cl.
*C12N 1/20* (2006.01)
*C12Q 1/00* (2006.01)
*C07N 21/02* (2006.01)
*C12P 21/06* (2006.01)
*A61K 38/00* (2006.01)

(52) U.S. Cl. .................. 435/252.34; 435/4; 435/5; 435/6; 435/69.1; 435/69.7; 435/252.3; 435/320.1; 530/300; 530/350; 536/23.4; 536/237; 514/44; 514/459; 424/190.1; 424/260.1

(58) Field of Classification Search ............... 435/69.1, 435/69.7, 252.3, 320.1, 4, 5, 6, 252.34; 424/260.1, 424/190.1; 514/44, 459; 536/23.4, 23.7; 530/300, 350
See application file for complete search history.

(56) References Cited

U.S. PATENT DOCUMENTS 6,551,795 B1 * 4/2003 Rubenfield et al. ........ 435/69.1

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129-2138, 1990).*
Database: PIR_80, Accession No. A83547.*
Altschul et al., Nucleic Acids Research (1997) 25(17):3389-3402.
BLAST search referenced in Altschul et al., Nucleic Acids Research (1997) 25(17):3389-3402.
Duplantier et al., Bioorganic and Medicinal Chemistry Letters (2001) 11:2593-2596.
International Search Report for PCT/US04/24051, mailed on Jan. 18, 2006, 4 pages.
Yoon et al., Developmental Cell (2002) 3:593-603.

* cited by examiner

*Primary Examiner*—Bruce R. Campell
*Assistant Examiner*—Padma Baskar
(74) *Attorney, Agent, or Firm*—Morrison & Foerster LLP

(57) ABSTRACT

A bacterial protein which converts 2-methyl citrate to 2-methyl isocitrate is a previously unknown target for antibacterial agents. The protein of this activity is associated with mucoid bacteria and inhibitors of production or activity of this protein in combination with propionic acid mitigate the virulence of these bacteria.

5 Claims, 8 Drawing Sheets

```
ATGAACAGCGCACACCGCAAACCGCTCCCCGGCACCCGCCTGGACTACTTCGACGCCCGCGAGGCGGTCGAGGCGATCCAGCCCGGCGCCTACGCCAAGC 100
 M  N  S  A  H  R  K  P  L  P  G  T  R  L  D  Y  F  D  A  R  E  A  V  E  A  I  Q  P  G  A  Y  A  K
TGCCCTATACCTCCCGCGTGCTCGCCGAGAACCTGGTGCGCCGCTGCGACCCGGCGACCCTGGAGGCTTCGCTGCGCCAACTGGTCGAGCGCAAGCGCGA 200
 L  P  Y  T  S  R  V  L  A  E  N  L  V  R  R  C  D  P  A  T  L  E  A  S  L  R  Q  L  V  E  R  K  R  D
CCTCGACTTCCCCTGGTACCCGGCGCGGGTGGTCTGCCATGACATCCTCGGGCAGACCGCGCTGGTCGACCTCGCCGGCCTGCGCGACGCCATCGCCGAC 300
  L  D  F  P  W  Y  P  A  R  V  V  C  H  D  I  L  G  Q  T  A  L  V  D  L  A  G  L  R  D  A  I  A  D
AAGGGCGGCGACCCGGCCCAGGTCAACCCGGTGGTGCCGGTGCAACTGATCGTCGACCACTCGCTGGCGGTGGAATGCGGCGGCTACGACCCCGAGGCCT 400
 K  G  G  D  P  A  Q  V  N  P  V  V  P  V  Q  L  I  V  D  H  S  L  A  V  E  C  G  G  Y  D  P  E  A
TCGCCAAGAACCGCGCCATCGAGGACCGCCGCAACGAGGACCGCTTCCACTTCATCGACTGGACCAAGCAGGCCTTCCGCAACGTCGACGTGATCCCGCC 500
 F  A  K  N  R  A  I  E  D  R  R  N  E  D  R  F  H  F  I  D  W  T  K  Q  A  F  R  N  V  D  V  I  P  P
GGGCAACGGCATCATGCACCAGATCAACCTGGAGAAAATGTCGCCGGTGATCCAGGCGCGCGACGGCGTGGCCTTCCCCGATACCTGCGTGGGCACCGAC 600
 G  N  G  I  M  H  Q  I  N  L  E  K  M  S  P  V  I  Q  A  R  D  G  V  A  F  P  D  T  C  V  G  T  D
AGCCATACCCCGCACGTCGACGCCCTGGGCGTGATCGCCATCGGCGTCGGCGGCCTGGAAGCGGAAAACGTGATGCTCGGCCGCGCCTCCTGGCTGCGCC 700
 S  H  R  R  H  V  D  A  L  G  V  I  A  I  G  V  G  G  L  E  A  E  N  V  M  L  G  R  A  S  W  M  R
TGCCGGACATCGTCGGCGTCGAGCTGAGCGGCCGTCGCCAGCCGGGCATCACCGCCACCGACGTGGTGCTGGCCCTGACCGAGTTCCTGCGCAAGCAGAA 800
 L  P  D  I  V  G  V  E  L  S  G  R  R  Q  P  G  I  T  A  T  D  V  V  L  A  L  T  E  F  L  R  K  Q  K
GGTGGTCGGCGCCTACCTGGAGTTCTACGGCGAAGGCGCCTCCAGCCTGACCCTCGGCGACCGCGCGACCATCTCCAACATGGCTCCGGAATACGGCGCC 900
  V  V  G  A  Y  L  E  F  Y  G  E  G  A  S  S  L  T  L  G  D  R  A  T  I  S  N  M  A  P  E  Y  G  A
ACCGCGGCGATGTTCGCCATCGACCAGCAGACCATCGACTACCTGCGCCTCACCGGCCGCGACGACGAGCAGGTCGCCCTGGTGGAGGCCTATGCGCGCA 1000
 T  A  A  M  F  A  I  D  Q  Q  T  I  D  Y  L  R  L  T  G  R  D  D  E  Q  V  A  L  V  E  A  Y  A  R
CCGCCGGACTCTGGGCCGACAGCCTGGTCGACGCCGAGTACGAGCGGGTACTGAAGTTCGACCTGTCCAGCGTGGTGCGCAACATGGCCGGCCCGTCCAA 1100
 T  A  G  L  W  A  D  S  L  V  D  A  E  Y  E  R  V  L  K  F  D  L  S  S  V  V  R  N  M  A  G  P  S  N
TCCGCACGCCAGGGTCGCCACCAGCGAACTGGCGGCGAAAGGCATCGCCGGCAACCTCGAGCGGGCCCGCGCCGAGGAAGCCGAGGGCCTGATGCCGGAC 1200
  P  H  A  R  V  A  T  S  E  L  A  A  K  G  I  A  G  N  L  E  R  A  R  A  E  E  A  E  G  L  M  P  D
GGCGCGGTGATCATCGCCGCGATCACCAGTTGCACCAACACCAGCAACCCGCGCAACGTGATCGCCGCCGGCCTGCTGGCGCGCAACGCCGACCGCCTCG 1300
 G  A  V  I  I  A  A  I  T  S  C  T  N  T  S  N  P  R  N  V  I  A  A  G  L  L  A  R  N  A  D  R  L
GCCTGGTCCGCAAGCCATGGGTGAAGACCTCGCTGGCACCCGGCTCCAAGGTGGTCACCGAATACCTGCGCGAAGCCGGCCTGCTGCCGCACCTGGAAGC 1400
 G  L  V  R  K  P  W  V  K  T  S  L  A  P  G  S  K  V  V  T  E  Y  L  R  E  A  G  L  L  P  H  L  E  A
CCTCGGCTTCGGCGTGGTGGCCTACGCCTGCACGTCTTGCAACGGCATGTCCGGCGCCCTCGACCCGGCGATCCAGCGGGAGATCGTCGAGCGCGACCTG 1500
 L  G  F  G  V  V  A  Y  A  C  T  S  C  N  G  M  S  G  A  L  D  P  A  I  Q  R  E  I  V  E  R  D  L
TACGCCACCGCGGTGCTCTCCGGCAACCGCAACTTCGACGGGCGCATCCACCCCTACGCCAAGCAGGCCTTCCTCGCCTCGCCGCCGCTGGTGGTGGCCT 1600
  Y  A  T  A  V  L  S  G  N  R  N  F  D  G  R  I  H  P  Y  A  K  Q  A  F  L  A  S  P  P  L  V  V  A
ACGCCATCGCCGGGACCATCCGCTTCGACATCGAGCGCGACGTGCTCGGCGTGGTGGACGGCAAGGAGATCCGCCTGAAGGACCTCTGGCCGAGCGACGA 1700
 Y  A  I  A  G  T  I  R  F  D  I  E  R  D  V  L  G  V  V  D  G  K  E  I  R  L  K  D  L  W  P  S  D  E
GGAGATCGACGCGGTGGTCAGGGCGGCGGTGAAGCCCGAGCAGTTCCGCCAGGTCTAGATCCCGATGTTCGACATCACCCACGGCGAGCGCGAGAAGGTC 1800
  E  I  D  A  V  V  R  A  A  V  K  P  E  Q  F  R  Q  V  Y  I  P  M  F  D  I  T  H  G  E  R  E  K  V
GACCCGCTCTACGCCTGGCGCCCGACGAGCACCTACATCCGCCGCCCGCCGTACTGGGAAGGCGCCCTCGCCGGCGAACGCACCCTGCGCGGCATGCGCC 1900
 D  P  L  Y  A  W  R  P  T  S  T  Y  I  R  R  P  P  Y  W  E  G  A  L  A  G  E  R  T  L  R  G  M  R
CGCTGGCGGTGCTGCCGGACAACATCACCACCGACCACCTGTCGCCGTCCAACGCCGATCCTCGCCGACAGTGCGGCAGGCGAATACCTGGCGAAAATGGG 2000
 P  L  A  V  L  P  D  N  I  T  T  D  H  L  S  P  S  N  A  I  L  A  D  S  A  A  G  E  Y  L  A  K  M  G
CCTGCCCGAGGAGGACTTCAACTCCTACGCCACCCACCGCGGCGACCACCTCACCGCGCAACGCGCGACCTTCGCCAACCCGAAGCTGTTCAACGAGATG 2100
  L  P  E  E  D  F  N  S  Y  A  T  H  R  G  D  H  L  T  A  Q  R  A  T  F  A  N  P  K  L  F  N  E  M
GTGCGCAACGCCGACGGCAGCGTGAAGCAGGGTTCGCTGGCGCGGGTCGAGCCGGAAGGCAAGGTGATGCGCATGTGGGAAGCCATCGAGACCTACATGG 2200
 V  R  N  A  D  G  S  V  K  Q  G  S  L  A  R  V  E  P  E  G  K  V  M  R  M  W  E  A  I  E  T  Y  M
AGCGCAAGCAGCCGCTGATCATCGTCGCCGGCGCCGACTACGGGCAGGGTTCTTCGCGCGACTGGGCGGCCAAGGGCGTGCGCCTGGCCGGGGTGGAGGC 2300
 E  R  K  Q  P  L  I  I  V  A  G  A  D  Y  G  Q  G  S  S  R  D  W  A  A  K  G  V  R  L  A  G  V  E  A
GATCGTCGCCGAGGGCTTCGAGCGCATCCACCGCACCAACCTGATCGGCATGGGCGTGCTGCCGCTGGAGTTCAAGCCGGGTACCACCCGCCTGACCCTG 2400
  I  V  A  E  G  F  E  R  I  H  R  T  N  L  I  G  M  G  V  L  P  L  E  F  K  P  G  T  T  R  L  T  L
GGGATCGACGGCAGCGAGACCTTCGACGTGCTCGGCGCTCGCCGGCCGCCGCCGACCTGACCCTGGTCATCCACCGGCGCGACGGGGAGCGGCTCGAAG 2500
 G  I  D  G  S  E  T  F  D  V  L  G  A  R  R  P  R  A  D  L  T  L  V  I  H  R  R  D  G  E  R  L  E
TGCCGGTGACCTGCCGCCTGGACAGCGACGAGGAAGTCTCCATCTACGAAGCCGGCGGCGTACTGCAACGCTTCGCCCAGGACTTCCTGGAGGCGGCCGG 2600
 V  P  V  T  C  R  L  D  S  D  E  E  V  S  I  Y  E  A  G  G  V  L  Q  R  F  A  Q  D  F  L  E  A  A  G
CGCCTGA 2607
 A
```

FIG. 2A

```
MNSAHRKPLPGTRLDYFDAREAVEAIQPGAYAKLPYTSRVLAENLVRRCDP
ATLEASLRQLVERKRDLDFPWYPARVVCHDILGQTALVDLAGLRDAIADKG
GDPAQVNPVVPVQLIVDHSLAVECGGYDPEAFAKNRAIEDRRNEDRFHFID
WTKQAFRNVDVIPPGNGIMHQINLEKMSPVIQARDGVAFPDTCVGTDSHRR
HVDALGVIAIGVGGLEAENVMLGRASWMRLPDIVGVELSGRRQPGITATDV
VLALTEFLRKQKVVGAYLEFYGEGASSLTLGDRATISNMAPEYGATAAMFA
IDQQTIDYLRLTGRDDEQVALVEAYARTAGLWADSLVDAEYERVLKFDLSS
VVRNMAGPSNPHARVATSELAAKGIAGNLERARAEEAEGLMPDGAVIIAAI
TSCTNTSNPRNVIAAGLLARNADRLGLVRKPWVKTSLAPGSKVVTEYLREA
GLLPHLEALGFGVVAYACTSCNGMSGALDPAIQREIVERDLYATAVLSGNR
NFDGRIHPYAKQAFLASPPLVVAYAIAGTIRFDIERDVLGVVDGKEIRLKD
LWPSDEEIDAVVRAAVKPEQFRQVYIPMFDITHGEREKVDPLYAWRPTSTY
IRRPPYWEGALAGERTLRGMRPLAVLPDNITTDHLSPSNAILADSAAGEYL
AKMGLPEEDFNSYATHRGDHLTAQRATFANPKLFNEMVRNADGSVKQGSLA
RVEPEGKVMRMWEAIETYMERKQPLIIVAGADYGQGSSRDWAAKGVRLAGV
EAIVAEGFERIHRTNLIGMGVLPLEFKPGTTRLTLGIDGSETFDVLGARRP
RADLTLVIHRRDGERLEVPVTCRLDSDEEVSIYEAGGVLQRFAQDFLEAAG
A
```

Figure 2B

```
     MNSAHRKPLPGT----RLDYFDARHAVEAIQPGAYAKLPYTSRVLAENLVRRCDP---ATLEASLRQIMERKRDLDFP----WYPARVVC  P. aeruginosa acnC
     NQSYRKPLPGT----DLEYMDARAACEDIKPGSMDKLPYTSPILSENLVARADKVDLPMLQSWLGQLIEGKQEIDF----PWYPARVVC  N. gonorrhoeae acnC
     NQRYRKPLPGT----DLEYMDARAACEGIKPGSMDKLPYTSPILAENLVRADKVDLPTIQSWLGQLIEGKQEIDF----PWYPARVVC  N. meningitidis acnC
     MNTKYRKNLPGT----SLDYFDAFQAVEDLQAGAWHLPYTSRVLAENLVRRCDP---ATLSDSIRQLIERRRDMFP-VPPWYPARVVC  B. pertussis acnC
     MNSLYRKAISPSPAQSQVDFFDIRAAVEALKPGAYQTLPYTARILAENLVRRCPPEQL---SESLLDQIIERKRDLDFP----WYPARVVC  V. cholerae acnC
     MNTQYRKPLPGT----ALDYFDIRDAIEAIAPGAYAKLPYTSRVLAENLVRRCEP---EMLTASLKQIIESKQELDF-P---WEPARVVC  S. putrefaciens acnC 0  HDILGQTALVDLAGLRDAIADKGGDPAQVNPVVPMQLIVDHSLAVEQGGYDPLDAFAKNRAIEDRRNEDRPHFIDWTKQAFRNVDVIPPGN  P. aeruginosa acnC
  2  HDILGQTALVDLAGLRDAIAEKGGDPAKVNPVVPQTQLIVDHSLAVEQGYDPDAFRKNFEIEDRRNEDRPHFINWTKTAFENVDVIPACN  N. gonorrhoeae acnC
  2  HDILGQTALVDLAGLRDAIAEKGGDPAKVNPVVPQTQLIVDHSLAVEQGYDPDAFRKNREIEDRRNEDRPHFINWTKTAFENVDVIPACN  N. meningitidis acnC
  4  HDILGQTALVDLAGLRDAIADAGGDPAQIINPVVPTQLIVDHSLAVEYPGFDKDAFMKNRAMEDRRNEDRPHFINWTKLAFNVDVIPPGN  B. pertussis acnC
  4  HDILGQTALVDLAGLRDAIAEQGGDPAQVNPVVETQLIVDHSLAVEYSGCDPDAFTKNRAMEDRRNEDRPHFIEWCKTAFNVSVIPAGN  V. cholerae acnC
  0  HDILGQTALVDLAGLRDAIAAKGGDPAQVNPVVPTQLIVDHSLAVEYGGFIKDAFAKNRAIEDRRNEDRPHFINWTQKAFKNLDVIPQCN  S. putrefaciens acnC 170  GIMHQINLEKMSPVIIQARDLGVAFPDTCVGTDSHRRHVDALGVIAIGVGGLEAEFVMLGRASWMRLPDIVGVELSGRRQPGITATDLVLAL  P. aeruginosa acnC
172  GIMHQINLEKMSPVVQVKNGVAFPDTCVGTDSHTPEVDALGVISVGVGGLEAETVMLGRASMMRLPDIVGVELNGKRQAGITATDVVLAL  N. gonorrhoeae acnC
172  GIMHQINLEKMSPVVQVKNGVAFPDTCVGTDSHTPEVDALGVISVGVGGLEAETVMLGRASMMRLPDIVGVELNGKRKAGITATDVVLAL  N. meningitidis acnC
174  GIMHQITLHKMSPVVQVPIDKAFPDTCVGTDSHTPFVDALGVIAIGVGGLEAEFWMLGRASWMRLPDIVGVELTGRPDAGITQTDVVLAL  B. pertussis acnC
174  GIMHQINLEKMSPVVQVKEIGVAFPDSCVGTDSHTPEVDALGVILAIGVGGLEAETVMLGRPSMMRLPDIVGVKLTGAROPGITATDVVLAL  V. cholerae acnC
170  GIMHQINLERMSPVIHARNGVAFPDTLVGTDSHTPEVDALGVIAIGVGGLEAESVMLGRASYMRLPDIIGVELTGKPQPGITATDVVLAL  S. putrefaciens acnC 260  TEFLRKQKVVGAYLEFIGEGASSLTLGDRATISNMAPEYGATAAMFAIDQQTIDYLRLTGRDDEQVALVEAYARTAGLWADSLVDHEYER  P. aeruginosa acnC
262  TEFLRKERVVGAFVEFFGEGARSLSLGDRATISNMTPEFGATAAMFAIDAQTIDYLKLTGRDDAQVKLVETYAKTAGLWAGGLKTAVYER  N. gonorrhoeae acnC
262  TEFLRKEPVVGAFVEFFGEGARSLSLGDRATISNMTPEFGATAAMFAIDEQTIDYLKLTGRDDAQVKLVETYAKTAGLWADDALKTAVYER  N. meningitidis acnC
263  TEFLRKEXWGAYLEFLGEGASALTIGDRATISNMTPEFGATAAMFMIDQTIDYLMLTGREDSQVKLVETYARQAGLWADDILAGPQYER  B. pertussis acnC
264  TEFLRKERNVGAYLEFFGEGAFALTIGDRATISNMTPEVGATAGMFMIDEQTIDYLLLTGREPEQVALVESYAKMAGLWADSLEHPEYER  V. cholerae acnC
260  TEFLRAQKVVSSYLEFFGEGATALTLGDRATISNMTPEFGATAAMFMTDQCTIDYLTLTGREAEQVKLVETYAKTAGLWSDDLKQAVYER  S. putrefaciens acnC 350  VLKFDLSSVVRNMAGPSNPHARVATSELAAKGIAGNLRRARAEEAEGLMPDGAVIIAAITSCTNTSNPRNVHAAGLLARNADRLGLMRKP  P. aeruginosa acnC
352  VLKFDLSSVIRNMAGPSNPHAREATADLAAKGLAKPYE----EPSDGQMPDGAVIIAAITSCTNTSNPRNVVAAALLARNANRLGLKRKP  N. gonorrhoeae acnC
352  VLKFDLSSVIRNMAGPSNPHAREATADLAGKGLAKPYE----EPSDGQMPDGAVIIAAITSCTNTSNPRNVVAAALLARNANRLGLQRKP  N. meningitidis acnC
353  MLRFDLSSVVRNMAGPSNPHKRVATTELAERGIAGPWQ-----EPPGQMPDGAVIIAAITSCTNTSNPRNVIAAALLARNANRPGLTRKP  B. pertussis acnC
354  VLEFDLSSVERNIAGPSNPHRRLPIKDLSARGIAIPAQQREAQQAEGLMPDGAVIIAAITSCTNTSNPRNVVAAGLLAKKANQLGLKRQP  V. cholerae acnC
350  TLHFDLSSVVRTIAGPSNPHARVPISELAAKGISGEVE-----NEPGLMPDGAVIIAAITSCTNTSNPRNVIAAGLLARNAMAKGLTRKP  S. putrefaciens acnC 440  WVKTSLAPGSKVVTEYILREAGLLPHLPALGFQVVAYACTSCNGMSGALDPAIQREIVERDLYATAVLSGNRNFDGRIHPYAKQAFLASPP  P. aeruginosa acnC
438  WVKSSFAPGSKVAGIYILKEAGLLPEMEKLGFGIVAFACTTCNGMSGALDPKIQQEIIDRDLYATAVLSGNRNFDGRIHPYAKQAFLASPP  N. gonorrhoeae acnC
438  WVKSSFAPGSKVAEIYILKEADLLPEMEKLGFGIVAFACTTCNGMSGALDPKIQKEIIDRDLYATAVLSGNRNFDGRIHPYAKQAFLASPP  N. meningitidis acnC
438  WVKSSLAPGSKAVQLYLEEAGLLPDIAKLGFGIVAFACTTQGMSGALDPKIWQEIIERDLYATAVLSNRNFDGRIHPYAKQAFLASPP  B. pertussis acnC
444  WVKTSFAPGSKVAKLYILQEAGLISELEQLGFGIVAFACTTCNGMSGALDPAIQQEIIERDLYATAVLSGNRNFDGRIHPYAKQAFLASPP  V. cholerae acnC
435  WVKTSLAPGSKAVQLYLEEANLLPELESLGFGIVGFACTTCNGMSGALDPMIQQEVIDRDLYATAVLSGNRNFDGRIHPYAKQAFLASPP  S. putrefaciens acnC
```

*FIG. 2C-1*

```
530 LVVAYAIAGTIRFDIERDVLGV-VDGKEIRLKDLWPSDEEIDAVVRAAVKPEQFRQVYIPMFDITHGEREKVDPLYAWRPLSTYIRRPPY   P. aeruginosa acnC
528 LVVAYALAGSIRFDIENDVLGV-ADGREIRIKDLWPTDEEIDAIVAEYVKPQQFRDLYIPMFDLGTAQKAP-SPLYDWRPMSTYIRRPPY  N. gonorrhoeae acnC
528 LVVAYALAGSIRFDIENDVLGV-ADGKEIRIKDLWPTDEEIDAIVAEYVKPQQFRDVYIPMFDLGTAQKAP-SPLYDWRPMSTYIRRPPY  N. meningtidis acnC
528 LVIIAYAIAGTMRFDIEKDALGVDARGKPVILKDLWPSDAEIDAVVTRSVKPEFRKVYEPMERFAQEQIGKVDPLYAWRPQSTYIRRPPY  B. pertussis acnC
534 LVVAYAIAGTMRFDIERDALGHDAQGKPLMLNHLWPSDEEIDAVVGRAVKPEQFKQIYIQMFKLDETQSASVSPLYDWRPMSTYIRRPPY  V. cholerae acnC
525 LVVAYAIAGTIRFDIEKDVLGLDKDGKPVRILNIWPSAEIDAVIAASVKPEQFRKVYEPMFDLSVDYGDKVSPLYDWRPQSTYIRRPPY   S. putrefaciens acnC 619 WEGALAGERTLRGMRPLAVLPDNITTDHLSPSNAILADSAAGEYLAKMGLPEEDFNSYATHRGDHLTAQRATFANPKLFNEMVRNADGSV  P. aeruginosa acnC
616 WEGALAGERTLRGMREPAILPDNITTDHLSPSNAILAGSAAGEYLAKMGLPEEDFNSYATHRGDHLTAQRATFANPKLFNEMVRNEDGSV  N. gonorrhoeae acnC
616 WEGALAGERTLSGMRPLAILPDNITTDHLSPSNAILASSAAGEYLAKMGLPEEDFNSYATHRGDHLTAQRATFANPKLFNEMVRNEDGSV  N. meningtidis acnC
618 WEGALAGERTIEGMRILAVLPDNITTDHLSPSNAIMADSAKGEYLAKMGLPEEDFNSYATHRGDHLTAQRATFANPKLINEMAV-VDGQW  B. pertussis acnC
623 WEGALAAERTLKAMRPLAILPDNITTDHLSPSNAILASSAAGEYIHKMGVPEEDFNSYATHRGDHLTAQRATFANPKLFNEMVKE-NQQI  V. cholerae acnC
615 WEGALAGERTLKGMRPLAVLPDNITTDHLSPSNAIPMDSAAGEYIHKMGLPEEDFNSYATHRGDHLTAQRATFANPKLNEMAI-VDGKW   S. putrefaciens acnC 709 KQGSLARVEPEGKVMRMWEAIETYNERKQPLIIVAGADYGQGSSRDWAAKGVRLAGVEAIVAEGFERIHRTNLIGMGVLPLEFKPGTIRL  P. aeruginosa acnC
706 RQGSLARVEPEGQTVRMWEAIETYMNRKQPLIIIAGADYGQGSSRDWAAKGVRLAGVEAIAAEGFERIHRTNLIGMGVLPLQFKPGTNRH  N. gonorrhoeae acnC
706 RQGSLARVEPEGQTVRMWEAIETYMNRKQPLIIIAGADYGQGSSRDWAAKGVRLAGVEAIVAEGFERIHRTNLIGMGVLPLQFKPGTNRH  N. meningtidis acnC
706 KQGSLARLEPEGKVMRMWETIETYMDRKQPLIIVAGADYGQGSSRDWAAKGVRLAGVEAIVAKGFERIHRTNLIGMGVLPLEFQAGVDRK  B. pertussis acnC
712 KQGSLARLEPEGKVTRMWEAIETYMNRKQPLIVIAGADYGQGSSRDWAAKGVRLAGVEAIVAEGFERIHRTNLVGMGVLPLEFKPGMNRH  V. cholerae acnC
704 KQGSLARLEPEGVVIRMWEAIETYMDRKQPLIIIAGADYGQGSSRDWAAKGVRLAGVEAIVAEGFERIHRTNLVGMGVLPLEFKPGENRA  S. putrefaciens acnC 899 TLGIDGSETFDVLGRRPRADLTLVIHRRDGERLEVPVTCRLDSDEEVSIYEAGGVLQRFAQDFLEAAGA.      P. aeruginosa acnC
896 TLQIDGSETIMDVVGERTPRCGLTLVIHRKNGETVEVPVTCREDTAEEAIVYEAGGVLQRFAQDFLEGN-AA   N. gonorrhoeae acnC
896 TLQIDGSETIMDVVGERTPRQDLTLVIHRKNGETVEVELTCRLDTAEEVLVYEAGGVLQRFAQDFLEGN-AA   N. meningtidis acnC
897 TLGIDGSETFDVVGERMPRATLTLVIHRRDGEQMQVPVLCRLDTAEEVSIYEAGGVLQRFAQDFLE----S    B. pertussis acnC
802 XLALDGTELFDVVGEIRPGADLALVVTRQNGEKLDMVVTCRLDTADEVHYQAGGVLQRFAQDFL           V. cholerae acnC
894 TMGIDGTEMFDVLGSIAPRADLTVILTRKNGERVEVPVTCRLDTAEEVSIYEAGGVLQRFAQDFLE----S    S. putrefaciens acnC
```

Decoration 'Decoration #1': Shade (with solid light yellow) residues that match the consensus named 'Consensus #1' exactly.

Decoration 'Decoration #2': Box resudues that match the Consensus exactly.

FIG. 2C-2

SEQUENCE LISTING

<160> NUMBER OF SEQ ID NOS: 12

<210> SEQ ID NO 1
<211> LENGTH: 21
<212> TYPE: PRT
<213> ORGANISM: Artificial Sequence
<220> FEATURE:
<223> OTHER INFORMATION: forward primer

<400> SEQUENCE: 1

Gly Thr Asn Gly Gly Asn Ala Cys Asn Gly Ala Tyr Thr Cys Asn Cys
 1               5                  10                  15

Ala Tyr Ala Cys Asn
            20

<210> SEQ ID NO 2
<211> LENGTH: 21
<212> TYPE: PRT
<213> ORGANISM: Artificial Sequence
<220> FEATURE:
<223> OTHER INFORMATION: reverse primer

<400> SEQUENCE: 2

Asn Cys Lys Asn Cys Cys Tyr Thr Cys Arg Ala Ala Arg Thr Thr Asn
 1               5                  10                  15

Cys Lys Arg Thr Thr
            20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
gtggcaccga cagccatac                                                  19

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
gcgcccgtcg aagttgcggt t                                               21

<210> SEQ ID NO 5
<211> LENGTH: 2607
<212> TYPE: DNA
<213> ORGANISM: P. aeruginosa

<400> SEQUENCE: 5
atgaacagcg cacaccgcaa accgctcccc ggcacccgcc tggactactt cgacgcccgc      60
gaggcggtcg aggcgatcca gcccggcgcc tacgccaagc tgccctatac ctcccgcgtg     120
ctcgccgaga acctggtgcg ccgctgcgac cggcgacccc tggaggcttc gctgcgccaa     180
ctggtcgagc gcaagcgcga cctcgacttc ccctggtacc cggcgcgggt ggtctgccat     240
gacatcctcg gcagaccgc gctggtcgac ctcgccggcc tgcgcgacgc catcgccgac     300
aagggcggcg acccggccca ggtcaacccg gtggtgccgg tgcaactgat cgtcgaccac     360

```
tcgctggcgg tggaatgcgg cggctacgac cccgaggcct tcgccaagaa ccgcgccatc      420
gaggaccgcc gcaacgagga ccgcttccac ttcatcgact ggaccaagca ggccttccgc      480
aacgtcgacg tgatcccgcc gggcaacggc atcatgcacc agatcaacct ggagaaaatg      540
tcgccggtga tccaggcgcg cgacggcgtg gccttcccg atacctgcgt gggcaccgac       600
agccataccc cgcacgtcga cgccctgggc gtgatcgcca tcggcgtcgg cggcctggaa      660
gcggaaaacg tgatgctcgg ccgcgcctcc tggatgcgcc tgccggacat cgtcggcgtc      720
gagctgagcg ccgtcgcca gccgggcatc accgccaccg acgtggtgct ggccctgacc       780
gagttcctgc gcaagcagaa ggtggtcggc gcctacctgg agttctacgg cgaaggcgcc      840
tccagcctga ccctcggcga ccgcgcgacc atctccaaca tggctccgga atacggcgcc      900
accgcggcga tgttcgccat cgaccagcag accatcgact acctgcgcct caccggccgc      960
gacgacgagc aggtcgccct ggtggaggcc tatgcgcgca ccgccggact ctgggccgac     1020
agcctggtcg acgccgagta cgagcgggta ctgaagttcg acctgtccag cgtggtgcgc     1080
aacatggccg gcccgtccaa tccgcacgcc agggtcgcca ccagcgaact ggcggcgaaa     1140
ggcatcgccg gcaacctcga gcgggcccgc gccgaggaag ccgagggcct gatgccggac     1200
ggcgcggtga tcatcgccgc gatcaccagt tgcaccaaca ccagcaaccc gcgcaacgtg     1260
atcgccgccg gcctgctggc gcgcaacgcc gaccgcctcg gcctggtccg caagccatgg     1320
gtgaagacct cgctggcacc cggctccaag gtggtcaccg aatacctgcg cgaagccggc     1380
ctgctgccgc acctggaagc cctcggcttc ggcgtggtgg cctacgcctg cacgtcttgc     1440
aacggcatgt ccggcgccct cgacccggcg atccagcggg agatcgtcga gcgcgacctg     1500
tacgccaccg cggtgctctc cggcaaccgc aacttcgacg ggcgcatcca ccctacgcc      1560 aagcaggcct tcctcgcctc gccgccgctg tggtggcct acgccatcgc cgggaccatc      1620
cgcttcgaca tcgagcgcga cgtgctcggc gtggtggacg caaggagat ccgcctgaag      1680 gacctctggc cgagcgacga ggagatcgac gcggtggtca gggcggcggt gaagcccgag     1740
cagttccgcc aggtctacat cccgatgttc gacatcaccc acggcgagcg cgagaaggtc     1800
gacccgctct acgcctggcg cccgacgagc acctacatcc gccgcccgcc gtactgggaa     1860
ggcgccctcg ccggcgaacg caccctgcgc ggcatgcgcc cgctggcggt gctgccggac     1920
aacatcacca ccgaccacct gtcgccgtcc aacgcgatcc tcgccgacag tgcggcaggc     1980
gaatacctgg cgaaaatggg cctgcccgag gaggacttca actcctacgc cacccaccgc     2040
ggcgaccacc tcaccgcgca acgcgcgacc ttcgccaacc cgaagctgtt caacgagatg     2100
gtgcgcaacg ccgacggcag cgtgaagcag ggttcgctgg cgcgggtcga gccggaaggc     2160
aaggtgatgc gcatgtggga agccatcgag acctacatgg agcgcaagca gccgctgatc     2220
atcgtcgccg cgccgactta cgggcagggt tcttcgcgcg actgggcggc caagggcgtg     2280
cgcctggccg gggtggaggc gatcgtcgcc gagggcttcg agcgcatcca ccgcaccaac     2340
ctgatcggca tggcgtgct gccgctggag ttcaagccgg gtaccacccg cctgaccctg      2400
gggatcgacg gcagcgagac cttcgacgtg ctcggcgctc gccggccgcg cgccgacctg     2460
accctggtca tccaccggcg cgacggggag cggctcgaag tgccggtgac ctgccgcctg     2520
gacagcgacg aggaagtctc catctacgaa gccggcggc tactgcaacg cttcgcccag      2580
gacttcctgg aggcggccgg cgcctga                                          2607
```

<210> SEQ ID NO 6

<211> LENGTH: 868
<212> TYPE: PRT
<213> ORGANISM: P. aeruginosa

<400> SEQUENCE: 6

```
Met Asn Ser Ala His Arg Lys Pro Leu Pro Gly Thr Arg Leu Asp Tyr
 1               5                  10                  15

Phe Asp Ala Arg Glu Ala Val Glu Ala Ile Gln Pro Gly Ala Tyr Ala
            20                  25                  30

Lys Leu Pro Tyr Thr Ser Arg Val Leu Ala Glu Asn Leu Val Arg Arg
        35                  40                  45

Cys Asp Pro Ala Thr Leu Glu Ala Ser Leu Arg Gln Leu Val Glu Arg
    50                  55                  60

Lys Arg Asp Leu Asp Phe Pro Trp Tyr Pro Ala Arg Val Val Cys His
65                  70                  75                  80

Asp Ile Leu Gly Gln Thr Ala Leu Val Asp Leu Ala Gly Leu Arg Asp
                85                  90                  95

Ala Ile Ala Asp Lys Gly Gly Asp Pro Ala Gln Val Asn Pro Val Val
            100                 105                 110

Pro Val Gln Leu Ile Val Asp His Ser Leu Ala Val Glu Cys Gly Gly
        115                 120                 125

Tyr Asp Pro Glu Ala Phe Ala Lys Asn Arg Ala Ile Glu Asp Arg Arg
    130                 135                 140

Asn Glu Asp Arg Phe His Phe Ile Asp Trp Thr Lys Gln Ala Phe Arg
145                 150                 155                 160

Asn Val Asp Val Ile Pro Pro Gly Asn Gly Ile Met His Gln Ile Asn
                165                 170                 175

Leu Glu Lys Met Ser Pro Val Ile Gln Ala Arg Asp Gly Val Ala Phe
            180                 185                 190

Pro Asp Thr Cys Val Gly Thr Asp Ser His Thr Pro His Val Asp Ala
        195                 200                 205

Leu Gly Val Ile Ala Ile Gly Val Gly Gly Leu Glu Ala Glu Asn Val
    210                 215                 220

Met Leu Gly Arg Ala Ser Trp Met Arg Leu Pro Asp Ile Val Gly Val
225                 230                 235                 240

Glu Leu Ser Gly Arg Arg Gln Pro Gly Ile Thr Ala Thr Asp Val Val
                245                 250                 255

Leu Ala Leu Thr Glu Phe Leu Arg Lys Gln Lys Val Val Gly Ala Tyr
            260                 265                 270

Leu Glu Phe Tyr Gly Glu Gly Ala Ser Ser Leu Thr Leu Gly Asp Arg
        275                 280                 285

Ala Thr Ile Ser Asn Met Ala Pro Glu Tyr Gly Ala Thr Ala Ala Met
    290                 295                 300

Phe Ala Ile Asp Gln Gln Thr Ile Asp Tyr Leu Arg Leu Thr Gly Arg
305                 310                 315                 320

Asp Asp Glu Gln Val Ala Leu Val Glu Ala Tyr Ala Arg Thr Ala Gly
                325                 330                 335

Leu Trp Ala Asp Ser Leu Val Asp Ala Glu Tyr Glu Arg Val Leu Lys
            340                 345                 350

Phe Asp Leu Ser Ser Val Val Arg Asn Met Ala Gly Pro Ser Asn Pro
        355                 360                 365

His Ala Arg Val Ala Thr Ser Glu Leu Ala Ala Lys Gly Ile Ala Gly
    370                 375                 380

Asn Leu Glu Arg Ala Arg Ala Glu Glu Ala Glu Gly Leu Met Pro Asp
```

-continued

```
            385                 390                 395                 400
Gly Ala Val Ile Ile Ala Ala Ile Thr Ser Cys Thr Asn Thr Ser Asn
                    405                 410                 415
Pro Arg Asn Val Ile Ala Ala Gly Leu Leu Ala Arg Asn Ala Asp Arg
                420                 425                 430
Leu Gly Leu Val Arg Lys Pro Trp Val Lys Thr Ser Leu Ala Pro Gly
            435                 440                 445
Ser Lys Val Val Thr Glu Tyr Leu Arg Glu Ala Gly Leu Leu Pro His
        450                 455                 460
Leu Glu Ala Leu Gly Phe Gly Val Val Ala Tyr Ala Cys Thr Ser Cys
465                 470                 475                 480
Asn Gly Met Ser Gly Ala Leu Asp Pro Ala Ile Gln Arg Glu Ile Val
                485                 490                 495
Glu Arg Asp Leu Tyr Ala Thr Ala Val Leu Ser Gly Asn Arg Asn Phe
                500                 505                 510
Asp Gly Arg Ile His Pro Tyr Ala Lys Gln Ala Phe Leu Ala Ser Pro
            515                 520                 525
Pro Leu Val Val Ala Tyr Ala Ile Ala Gly Thr Ile Arg Phe Asp Ile
        530                 535                 540
Glu Arg Asp Val Leu Gly Val Val Asp Gly Lys Glu Ile Arg Leu Lys
545                 550                 555                 560
Asp Leu Trp Pro Ser Asp Glu Glu Ile Asp Ala Val Val Arg Ala Ala
                565                 570                 575
Val Lys Pro Glu Gln Phe Arg Gln Val Tyr Ile Pro Met Phe Asp Ile
                580                 585                 590
Thr His Gly Glu Arg Glu Lys Val Asp Pro Leu Tyr Ala Trp Arg Pro
            595                 600                 605
Thr Ser Thr Tyr Ile Arg Arg Pro Tyr Trp Glu Gly Ala Leu Ala
        610                 615                 620
Gly Glu Arg Thr Leu Arg Gly Met Arg Pro Leu Ala Val Leu Pro Asp
625                 630                 635                 640
Asn Ile Thr Thr Asp His Leu Ser Pro Ser Asn Ala Ile Leu Ala Asp
                645                 650                 655
Ser Ala Ala Gly Glu Tyr Leu Ala Lys Met Gly Leu Pro Glu Glu Asp
                660                 665                 670
Phe Asn Ser Tyr Ala Thr His Arg Gly Asp His Leu Thr Ala Gln Arg
            675                 680                 685
Ala Thr Phe Ala Asn Pro Lys Leu Phe Asn Glu Met Val Arg Asn Ala
        690                 695                 700
Asp Gly Ser Val Lys Gln Gly Ser Leu Ala Arg Val Glu Pro Glu Gly
705                 710                 715                 720
Lys Val Met Arg Met Trp Glu Ala Ile Glu Thr Tyr Met Glu Arg Lys
                725                 730                 735
Gln Pro Leu Ile Ile Val Ala Gly Ala Asp Tyr Gly Gln Gly Ser Ser
            740                 745                 750
Arg Asp Trp Ala Ala Lys Gly Val Arg Leu Ala Gly Val Glu Ala Ile
        755                 760                 765
Val Ala Glu Gly Phe Glu Arg Ile His Arg Thr Asn Leu Ile Gly Met
        770                 775                 780
Gly Val Leu Pro Leu Glu Phe Lys Pro Gly Thr Thr Arg Leu Thr Leu
785                 790                 795                 800
Gly Ile Asp Gly Ser Glu Thr Phe Asp Val Leu Gly Ala Arg Arg Pro
                805                 810                 815
```

-continued

```
Arg Ala Asp Leu Thr Leu Val Ile His Arg Arg Asp Gly Glu Arg Leu
            820                 825                 830

Glu Val Pro Val Thr Cys Arg Leu Asp Ser Asp Glu Glu Val Ser Ile
            835                 840                 845

Tyr Glu Ala Gly Gly Val Leu Gln Arg Phe Ala Gln Asp Phe Leu Glu
    850                 855                 860

Ala Ala Gly Ala
865

<210> SEQ ID NO 7
<211> LENGTH: 868
<212> TYPE: PRT
<213> ORGANISM: P. aeruginosa

<400> SEQUENCE: 7

Met Asn Ser Ala His Arg Lys Pro Leu Pro Gly Thr Arg Leu Asp Tyr
  1               5                  10                  15

Phe Asp Ala Arg Glu Ala Val Glu Ala Ile Gln Pro Gly Ala Tyr Ala
             20                  25                  30

Lys Leu Pro Tyr Thr Ser Arg Val Leu Ala Glu Asn Leu Val Arg Arg
         35                  40                  45

Cys Asp Pro Ala Thr Leu Glu Ala Ser Leu Arg Gln Leu Val Glu Arg
     50                  55                  60

Lys Arg Asp Leu Asp Phe Pro Trp Tyr Pro Ala Arg Val Val Cys His
 65                  70                  75                  80

Asp Ile Leu Gly Gln Thr Ala Leu Val Asp Leu Ala Gly Leu Arg Asp
                 85                  90                  95

Ala Ile Ala Asp Lys Gly Gly Asp Pro Ala Gln Val Asn Pro Val Val
            100                 105                 110

Pro Val Gln Leu Ile Val Asp His Ser Leu Ala Val Glu Cys Gly Gly
            115                 120                 125

Tyr Asp Pro Glu Ala Phe Ala Lys Asn Arg Ala Ile Glu Asp Arg Arg
    130                 135                 140

Asn Glu Asp Arg Phe His Phe Ile Asp Trp Thr Lys Gln Ala Phe Arg
145                 150                 155                 160

Asn Val Asp Val Ile Pro Pro Gly Asn Gly Ile Met His Gln Ile Asn
                165                 170                 175

Leu Glu Lys Met Ser Pro Val Ile Gln Ala Arg Asp Gly Val Ala Phe
            180                 185                 190

Pro Asp Thr Cys Val Gly Thr Asp Ser His Thr Pro His Val Asp Ala
            195                 200                 205

Leu Gly Val Ile Ala Ile Gly Val Gly Gly Leu Glu Ala Glu Asn Val
    210                 215                 220

Met Leu Gly Arg Ala Ser Trp Met Arg Leu Pro Asp Ile Val Gly Val
225                 230                 235                 240

Glu Leu Ser Gly Arg Arg Gln Pro Gly Ile Thr Ala Thr Asp Val Val
                245                 250                 255

Leu Ala Leu Thr Glu Phe Leu Arg Lys Gln Lys Val Val Gly Ala Tyr
            260                 265                 270

Leu Glu Phe Tyr Gly Glu Gly Ala Ser Ser Leu Thr Leu Gly Asp Arg
            275                 280                 285

Ala Thr Ile Ser Asn Met Ala Pro Glu Tyr Gly Ala Thr Ala Ala Met
    290                 295                 300

Phe Ala Ile Asp Gln Gln Thr Ile Asp Tyr Leu Arg Leu Thr Gly Arg
```

-continued

```
              305                 310                 315                 320
        Asp Asp Glu Gln Val Ala Leu Val Glu Ala Tyr Ala Arg Thr Ala Gly
                        325                 330                 335
        Leu Trp Ala Asp Ser Leu Val Asp Ala Glu Tyr Glu Arg Val Leu Lys
                        340                 345                 350
        Phe Asp Leu Ser Ser Val Val Arg Asn Met Ala Gly Pro Ser Asn Pro
                        355                 360                 365
        His Ala Arg Val Ala Thr Ser Glu Leu Ala Ala Lys Gly Ile Ala Gly
                        370                 375                 380
        Asn Leu Glu Arg Ala Arg Ala Glu Glu Ala Glu Gly Leu Met Pro Asp
        385                 390                 395                 400
        Gly Ala Val Ile Ile Ala Ala Ile Thr Ser Cys Thr Asn Thr Ser Asn
                        405                 410                 415
        Pro Arg Asn Val Ile Ala Ala Gly Leu Leu Ala Arg Asn Ala Asp Arg
                        420                 425                 430
        Leu Gly Leu Val Arg Lys Pro Trp Val Lys Thr Ser Leu Ala Pro Gly
                        435                 440                 445
        Ser Lys Val Val Thr Glu Tyr Leu Arg Glu Ala Gly Leu Leu Pro His
        450                 455                 460
        Leu Glu Ala Leu Gly Phe Gly Val Val Ala Tyr Ala Cys Thr Ser Cys
        465                 470                 475                 480
        Asn Gly Met Ser Gly Ala Leu Asp Pro Ala Ile Gln Arg Glu Ile Val
                        485                 490                 495
        Glu Arg Asp Leu Tyr Ala Thr Ala Val Leu Ser Gly Asn Arg Asn Phe
                        500                 505                 510
        Asp Gly Arg Ile His Pro Tyr Ala Lys Gln Ala Phe Leu Ala Ser Pro
                        515                 520                 525
        Pro Leu Val Val Ala Tyr Ala Ile Ala Gly Thr Ile Arg Phe Asp Ile
                        530                 535                 540
        Glu Arg Asp Val Leu Gly Val Val Asp Gly Lys Glu Ile Arg Leu Lys
        545                 550                 555                 560
        Asp Leu Trp Pro Ser Asp Glu Glu Ile Asp Ala Val Val Arg Ala Ala
                        565                 570                 575
        Val Lys Pro Glu Gln Phe Arg Gln Val Tyr Ile Pro Met Phe Asp Ile
                        580                 585                 590
        Thr His Gly Glu Arg Glu Lys Val Asp Pro Leu Tyr Ala Trp Arg Pro
                        595                 600                 605
        Thr Ser Thr Tyr Ile Arg Arg Pro Pro Tyr Trp Glu Gly Ala Leu Ala
                        610                 615                 620
        Gly Glu Arg Thr Leu Arg Gly Met Arg Pro Leu Ala Val Leu Pro Asp
        625                 630                 635                 640
        Asn Ile Thr Thr Asp His Leu Ser Pro Ser Asn Ala Ile Leu Ala Asp
                        645                 650                 655
        Ser Ala Ala Gly Glu Tyr Leu Ala Lys Met Gly Leu Pro Glu Glu Asp
                        660                 665                 670
        Phe Asn Ser Tyr Ala Thr His Arg Gly Asp His Leu Thr Ala Gln Arg
                        675                 680                 685
        Ala Thr Phe Ala Asn Pro Lys Leu Phe Asn Glu Met Val Arg Asn Ala
                        690                 695                 700
        Asp Gly Ser Val Lys Gln Gly Ser Leu Ala Arg Val Glu Pro Glu Gly
        705                 710                 715                 720
        Lys Val Met Arg Met Trp Glu Ala Ile Glu Thr Tyr Met Glu Arg Lys
                        725                 730                 735
```

```
Gln Pro Leu Ile Ile Val Ala Gly Ala Asp Tyr Gly Gln Gly Ser Ser
            740                 745                 750

Arg Asp Trp Ala Ala Lys Gly Val Arg Leu Ala Gly Val Glu Ala Ile
            755                 760                 765

Val Ala Glu Gly Phe Glu Arg Ile His Arg Thr Asn Leu Ile Gly Met
            770                 775                 780

Gly Val Leu Pro Leu Glu Phe Lys Pro Gly Thr Thr Arg Leu Thr Leu
785                 790                 795                 800

Gly Ile Asp Gly Ser Glu Thr Phe Asp Val Leu Gly Ala Arg Arg Pro
            805                 810                 815

Arg Ala Asp Leu Thr Leu Val Ile His Arg Arg Asp Gly Glu Arg Leu
            820                 825                 830

Glu Val Pro Val Thr Cys Arg Leu Asp Ser Asp Glu Glu Val Ser Ile
            835                 840                 845

Tyr Glu Ala Gly Val Leu Gln Arg Phe Ala Gln Asp Phe Leu Glu
            850                 855                 860

Ala Ala Gly Ala
865

<210> SEQ ID NO 8
<211> LENGTH: 867
<212> TYPE: PRT
<213> ORGANISM: N. gonorrhoeae

<400> SEQUENCE: 8

Asn Gln Ser Tyr Arg Lys Pro Leu Pro Gly Thr Asp Leu Glu Tyr Tyr
1               5                   10                  15

Asp Ala Arg Ala Ala Cys Glu Asp Ile Lys Pro Gly Ser Tyr Asp Lys
            20                  25                  30

Leu Pro Tyr Thr Ser Arg Ile Leu Ser Glu Asn Leu Val Asn Arg Ala
            35                  40                  45

Asp Lys Val Asp Leu Pro Met Ile Gln Ser Trp Leu Gly Gln Leu Ile
        50                  55                  60

Glu Gly Lys Gln Glu Ile Asp Phe Pro Trp Tyr Pro Ala Arg Val Val
65                  70                  75                  80

Cys His Asp Ile Leu Gly Gln Thr Ala Leu Val Asp Leu Ala Gly Leu
            85                  90                  95

Arg Asp Ala Ile Ala Glu Lys Gly Gly Asp Pro Ala Lys Val Asn Pro
            100                 105                 110

Val Val Gln Thr Gln Leu Ile Val Asp His Ser Leu Ala Val Glu Cys
            115                 120                 125

Gly Gly Tyr Asp Pro Asp Ala Phe Arg Lys Asn Arg Glu Ile Glu Asp
        130                 135                 140

Arg Arg Asn Glu Asp Arg Phe His Phe Ile Asn Trp Thr Lys Thr Ala
145                 150                 155                 160

Phe Glu Asn Val Asp Val Ile Pro Ala Gly Asn Gly Ile Met His Gln
            165                 170                 175

Ile Asn Leu Glu Lys Glu Met Ser Pro Val Val Gln Val Lys Asn Gly
            180                 185                 190

Val Ala Phe Pro Asp Thr Cys Val Gly Thr Asp Ser His Thr Pro His
            195                 200                 205

Val Asp Ala Leu Gly Val Ile Ser Val Gly Val Gly Gly Leu Glu Ala
        210                 215                 220

Glu Thr Val Met Leu Gly Arg Ala Ser Met Met Arg Leu Pro Asp Ile
```

```
            225                 230                 235                 240
Val Gly Val Glu Leu Thr Gly Lys Arg Gln Ala Gly Ile Thr Ala Thr
                245                 250                 255
Asp Ile Val Leu Ala Leu Thr Glu Phe Leu Arg Lys Glu Arg Val Val
                260                 265                 270
Gly Ala Phe Val Glu Phe Phe Gly Glu Gly Ala Arg Ser Ile Ser Ile
                275                 280                 285
Gly Asp Arg Ala Thr Ile Ser Asn Met Thr Pro Glu Phe Gly Ala Thr
                290                 295                 300
Ala Ala Met Phe Ala Ile Asp Ala Gln Thr Ile Asp Tyr Leu Lys Leu
305                 310                 315                 320
Thr Gly Arg Asp Asp Ala Gln Val Lys Leu Val Glu Thr Tyr Ala Lys
                325                 330                 335
Thr Ala Gly Leu Trp Ala Gly Gly Leu Lys Thr Ala Val Tyr Arg Arg
                340                 345                 350
Val Leu Lys Phe Asp Leu Ser Ser Val Thr Arg Asn Met Ala Gly Pro
                355                 360                 365
Ser Asn Pro His Ala Arg Phe Ala Thr Ala Asp Leu Ala Ala Lys Gly
                370                 375                 380
Leu Ala Lys Pro Tyr Glu Glu Pro Ser Asp Gly Gln Met Pro Asp Gly
385                 390                 395                 400
Ala Val Ile Ile Ala Ala Ile Thr Ser Cys Thr Asn Thr Ser Asn Pro
                405                 410                 415
Arg Asn Val Val Ala Ala Leu Leu Ala Arg Asn Ala Asn Pro Leu
                420                 425                 430
Gly Leu Lys Arg Lys Pro Trp Val Lys Ser Ser Phe Ala Pro Gly Ser
                435                 440                 445
Lys Val Ala Gly Ile Tyr Leu Lys Glu Ala Gly Leu Leu Pro Glu Met
                450                 455                 460
Glu Lys Leu Gly Phe Gly Ile Val Ala Phe Ala Cys Thr Thr Cys Asn
465                 470                 475                 480
Gly Met Ser Gly Ala Leu Asp Pro Lys Ile Gln Gln Glu Ile Ile Asp
                485                 490                 495
Arg Asp Leu Tyr Ala Thr Ala Val Leu Ser Gly Asn Arg Asn Phe Asp
                500                 505                 510
Gly Arg Ile His Pro Tyr Ala Lys Gln Ala Phe Leu Ala Ser Pro Pro
                515                 520                 525
Leu Val Val Ala Tyr Ala Leu Ala Gly Ser Ile Arg Phe Asp Ile Glu
                530                 535                 540
Asn Asp Val Leu Gly Val Ala Asp Gly Arg Glu Ile Arg Leu Lys Asp
545                 550                 555                 560
Ile Trp Pro Thr Asp Glu Glu Ile Asp Ala Ile Val Ala Glu Tyr Val
                565                 570                 575
Lys Pro Gln Gln Phe Arg Asp Ile Tyr Ile Pro Met Ser Asp Thr Gly
                580                 585                 590
Thr Ala Gln Lys Ala Pro Ser Pro Leu Tyr Asp Trp Arg Pro Met Ser
                595                 600                 605
Thr Tyr Ile Arg Arg Pro Pro Tyr Trp Glu Gly Ala Leu Ala Gly Glu
                610                 615                 620
Arg Thr Leu Arg Gly Met Arg Pro Ala Ile Leu Pro Asp Asn Ile
625                 630                 635                 640
Thr Thr Asp His Ile Ser Pro Ser Asn Ala Ile Leu Ala Gly Ser Ala
                645                 650                 655
```

-continued

Ala Gly Glu Tyr Leu Ala Lys Met Gly Leu Pro Glu Asp Phe Asn
            660             665             670

Ser Tyr Ala Thr His Arg Gly Asp His Leu Thr Ala Gln Arg Ala Thr
        675                 680                 685

Phe Ala Asn Pro Lys Leu Phe Asn Glu Met Val Cys Arg Asn Glu Asp
    690                 695                 700

Gly Ser Val Arg Gln Gly Ser Leu Ala Arg Val Glu Pro Glu Gly Gln
705                 710                 715                 720

Thr Met Arg Met Trp Glu Ala Ile Glu Thr Tyr Met Asn Arg Lys Gln
                725                 730                 735

Pro Leu Ile Ile Ile Ala Gly Ala Asp Tyr Gly Gln Gly Ser Ser Arg
                740                 745                 750

Asp Trp Ala Ala Lys Gly Val Arg Leu Ala Gly Val Glu Ala Ile Ala
        755                 760                 765

Ala Glu Gly Phe Glu Arg Ile His Arg Thr Asn Leu Ile Gly Met Gly
    770                 775                 780

Val Leu Pro Leu Gln Phe Lys Pro Gly Thr Asn Arg His Thr Leu Gln
785                 790                 795                 800

Leu Asp Gly Thr Glu Thr Tyr Asp Val Val Gly Glu Arg Thr Pro Arg
                805                 810                 815

Cys Gly Leu Thr Leu Val Ile His Arg Lys Asn Gly Thr Val Glu
                820                 825                 830

Val Pro Val Thr Cys Arg Pro Asp Thr Ala Glu Glu Ala Leu Val Tyr
                835                 840                 845

Glu Ala Gly Gly Val Leu Gln Arg Phe Ala Gln Asp Phe Leu Glu Gly
    850                 855                 860

Asn Ala Ala
865

<210> SEQ ID NO 9
<211> LENGTH: 865
<212> TYPE: PRT
<213> ORGANISM: N. meningitidis

<400> SEQUENCE: 9

Asn Gln Arg Tyr Arg Lys Pro Leu Pro Gly Thr Asp Leu Glu Tyr Tyr
1               5                   10                  15

Asp Ala Arg Ala Ala Cys Glu Gly Ile Lys Pro Gly Ser Tyr Asp Lys
                20                  25                  30

Leu Pro Tyr Thr Ser Arg Ile Leu Ala Glu Asn Leu Val Asn Arg Ala
            35                  40                  45

Asp Lys Val Asp Leu Pro Thr Leu Gln Ser Trp Leu Gly Gln Leu Ile
        50                  55                  60

Glu Gly Lys Gln Glu Ile Asp Phe Pro Trp Tyr Pro Ala Arg Val Val
65                  70                  75                  80

Cys His Asp Ile Leu Gly Gln Thr Ala Leu Val Asp Leu Ala Gly Leu
                85                  90                  95

Arg Asp Ala Ile Ala Glu Lys Gly Gly Asp Pro Ala Lys Val Asn Pro
            100                 105                 110

Val Val Gln Thr Gln Leu Ile Val Asp His Ser Leu Ala Val Glu Cys
        115                 120                 125

Gly Gly Tyr Asp Pro Asp Ala Phe Arg Lys Asn Arg Glu Ile Glu Asp
    130                 135                 140

Arg Arg Asn Glu Asp Arg Phe His Phe Ile Asn Trp Thr Lys Thr Ala

-continued

```
            145                 150                 155                 160
        Phe Glu Asn Val Asp Val Ile Pro Ala Gly Asn Gly Ile Met His Gln
                        165                 170                 175
        Ile Asn Leu Glu Lys Met Ser Pro Val Val Gln Val Lys Asn Gly Val
                    180                 185                 190
        Ala Phe Pro Asp Thr Cys Val Gly Thr Asp Ser His Thr Pro His Val
                    195                 200                 205
        Asp Ala Leu Gly Val Ile Ser Val Gly Val Gly Leu Glu Ala Glu
                210                 215                 220
        Thr Val Met Leu Gly Arg Ala Ser Met Met Arg Leu Pro Asp Ile Val
        225                 230                 235                 240
        Gly Val Glu Leu Asn Gly Lys Arg Lys Ala Gly Ile Thr Ala Thr Asp
                        245                 250                 255
        Ile Val Leu Ala Leu Thr Glu Phe Leu Arg Lys Glu Arg Val Val Gly
                    260                 265                 270
        Ala Phe Val Glu Phe Phe Gly Glu Gly Ala Arg Ser Leu Ser Ile Gly
                    275                 280                 285
        Asp Arg Ala Thr Ile Ser Asn Met Thr Pro Glu Phe Gly Ala Thr Ala
                290                 295                 300
        Ala Met Phe Ala Ile Asp Glu Gln Thr Ile Asp Tyr Leu Lys Leu Thr
        305                 310                 315                 320
        Gly Arg Asp Asp Ala Gln Val Lys Leu Val Glu Thr Tyr Ala Lys Thr
                        325                 330                 335
        Ala Gly Leu Trp Ala Asp Ala Leu Lys Thr Ala Val Tyr Pro Arg Val
                    340                 345                 350
        Leu Lys Phe Asp Leu Ser Ser Val Thr Arg Asn Met Ala Gly Pro Ser
                    355                 360                 365
        Asn Pro His Ala Arg Phe Ala Thr Ala Asp Leu Ala Gly Lys Gly Leu
                370                 375                 380
        Ala Lys Pro Tyr Glu Glu Pro Ser Asp Gly Gln Met Pro Asp Gly Ala
        385                 390                 395                 400
        Val Ile Ile Ala Ala Ile Thr Ser Cys Thr Asn Thr Ser Asn Pro Arg
                        405                 410                 415
        Asn Val Val Ala Ala Ala Leu Leu Ala Arg Asn Ala Asn Arg Leu Gly
                    420                 425                 430
        Leu Gln Arg Lys Pro Trp Val Lys Ser Ser Phe Ala Pro Gly Ser Lys
                    435                 440                 445
        Val Ala Glu Ile Tyr Leu Lys Glu Ala Asp Leu Leu Pro Glu Met Glu
                450                 455                 460
        Lys Leu Gly Phe Gly Ile Val Ala Phe Ala Cys Thr Thr Cys Asn Gly
        465                 470                 475                 480
        Met Ser Gly Ala Leu Asp Pro Lys Ile Gln Lys Glu Ile Ile Asp Arg
                        485                 490                 495
        Asp Leu Tyr Ala Thr Ala Val Leu Ser Gly Asn Arg Asn Phe Asp Gly
                    500                 505                 510
        Arg Ile His Pro Tyr Ala Lys Gln Ala Phe Leu Ala Ser Pro Pro Leu
                    515                 520                 525
        Val Val Ala Tyr Ala Leu Ala Gly Ser Ile Arg Phe Asp Ile Glu Asn
                530                 535                 540
        Asp Val Leu Gly Val Asp Gly Lys Glu Ile Arg Leu Lys Asp Ile
        545                 550                 555                 560
        Trp Pro Thr Asp Glu Glu Ile Asp Ala Ile Val Ala Glu Tyr Val Lys
                        565                 570                 575
```

-continued

```
Pro Gln Gln Phe Arg Asp Val Tyr Ile Pro Met Phe Asp Thr Gly Thr
            580                 585                 590

Ala Gln Lys Ala Pro Ser Pro Leu Tyr Asp Trp Arg Pro Met Ser Thr
        595                 600                 605

Tyr Ile Arg Arg Pro Pro Tyr Trp Glu Gly Ala Leu Ala Gly Glu Arg
    610                 615                 620

Thr Leu Ser Gly Met Arg Pro Leu Ala Ile Leu Pro Asp Asn Ile Thr
625                 630                 635                 640

Thr Asp His Leu Ser Pro Ser Asn Ala Ile Leu Ala Ser Ser Ala Ala
                645                 650                 655

Gly Glu Tyr Leu Ala Lys Met Gly Leu Pro Glu Glu Asp Phe Asn Ser
            660                 665                 670

Tyr Ala Thr His Arg Gly Asp His Leu Thr Ala Gln Arg Ala Thr Phe
        675                 680                 685

Ala Asn Pro Lys Leu Phe Asn Glu Met Val Arg Asn Glu Asp Gly Ser
    690                 695                 700

Val Arg Gln Gly Ser Leu Ala Arg Val Glu Pro Glu Gly Gln Thr Met
705                 710                 715                 720

Arg Met Trp Glu Ala Ile Glu Thr Tyr Met Asn Arg Lys Gln Pro Leu
                725                 730                 735

Ile Ile Ile Ala Gly Ala Asp Tyr Gly Gln Gly Ser Ser Arg Asp Trp
            740                 745                 750

Ala Ala Lys Gly Val Arg Leu Ala Gly Val Glu Ala Ile Val Ala Glu
        755                 760                 765

Gly Phe Glu Arg Ile His Arg Thr Asn Leu Ile Gly Met Gly Val Leu
    770                 775                 780

Pro Leu Gln Phe Lys Pro Gly Thr Asn Arg His Thr Leu Gln Leu Asp
785                 790                 795                 800

Gly Thr Glu Thr Tyr Asp Val Val Gly Glu Arg Thr Pro Arg Cys Asp
                805                 810                 815

Leu Thr Leu Val Ile His Arg Lys Asn Gly Glu Thr Val Glu Val Pro
            820                 825                 830

Ile Thr Cys Arg Leu Asp Thr Ala Glu Glu Val Leu Val Tyr Glu Ala
        835                 840                 845

Gly Gly Val Leu Gln Arg Phe Ala Gln Asp Phe Leu Glu Gly Asn Ala
    850                 855                 860

Ala
865

<210> SEQ ID NO 10
<211> LENGTH: 860
<212> TYPE: PRT
<213> ORGANISM: B. Pertussis

<400> SEQUENCE: 10

Met Asn Thr Lys Tyr Arg Lys Asn Leu Pro Gly Thr Ser Leu Asp Tyr
 1               5                  10                  15

Phe Asp Ala Arg Gln Ala Val Glu Asp Leu Gln Ala Gly Ala Trp Ala
            20                  25                  30

Thr Leu Pro Tyr Thr Ser Arg Val Leu Ala Glu Asn Leu Val Arg Arg
        35                  40                  45

Cys Asp Pro Ala Thr Leu Ser Asp Ser Leu Arg Gln Leu Ile Glu Arg
    50                  55                  60

Arg Arg Asp Met Asp Phe Pro Trp Tyr Pro Ala Arg Val Val Cys His
```

```
             65                  70                  75                  80
Asp Ile Leu Gly Gln Thr Ala Leu Val Asp Leu Ala Gly Leu Arg Asp
                 85                  90                  95
Ala Ile Ala Asp Ala Gly Gly Asp Pro Ala Gln Ile Asn Pro Val Val
                100                 105                 110
Pro Thr Gln Leu Ile Val Asp His Ser Leu Ala Val Glu Tyr Pro Gly
                115                 120                 125
Phe Asp Lys Asp Ala Phe Glu Lys Asn Arg Ala Val Glu Asp Arg Arg
                130                 135                 140
Asn Glu Asp Arg Phe His Phe Ile Asn Trp Thr Lys Leu Ala Phe Arg
145                 150                 155                 160
Asn Val Asp Val Ile Pro Pro Gly Asn Gly Ile Met His Gln Ile Asn
                165                 170                 175
Leu Glu Lys Met Ser Pro Val Val Gln Val Arg Asp Gly Met Ala Phe
                180                 185                 190
Pro Asp Thr Cys Val Gly Thr Asp Ser His Thr Pro His Val Asp Ala
                195                 200                 205
Leu Gly Val Ile Ala Ile Gly Val Gly Gly Leu Glu Ala Glu Asn Val
                210                 215                 220
Met Leu Gly Arg Ala Ser Trp Met Arg Leu Pro Asp Ile Val Gly Val
225                 230                 235                 240
Glu Leu Thr Gly Arg Pro Gln Ala Gly Ile Thr Cys Thr Asp Ile Val
                245                 250                 255
Leu Ala Leu Thr Glu Phe Leu Arg Arg Glu Lys Val Val Gly Ala Tyr
                260                 265                 270
Leu Glu Phe Leu Gly Glu Gly Ala Ser Ala Leu Thr Ile Gly Asp Arg
                275                 280                 285
Ala Thr Ile Ser Asn Met Thr Pro Glu Phe Gly Ala Thr Ala Ala Met
                290                 295                 300
Phe Tyr Ile Asp Gly Gln Thr Thr Asp Tyr Leu Thr Leu Thr Gly Arg
305                 310                 315                 320
Glu Asp Ser Gln Val Lys Leu Val Glu Thr Tyr Ala Arg Gln Ala Gly
                325                 330                 335
Leu Trp Ala Asp Asp Leu Ala Gly Ala Gln Tyr Glu Arg Met Leu Arg
                340                 345                 350
Phe Asp Leu Ser Ser Val Val Arg Asn Met Ala Gly Pro Ser Asn Pro
                355                 360                 365
His Lys Arg Val Ala Thr Thr Glu Leu Ala Glu Arg Gly Ile Ala Gly
                370                 375                 380
Pro Trp Gln Glu Thr Pro Gly Gln Met Pro Asp Gly Ala Val Ile Ile
385                 390                 395                 400
Ala Ala Ile Thr Ser Cys Thr Asn Thr Ser Asn Pro Arg Asn Val Ile
                405                 410                 415
Ala Ala Ala Leu Leu Ala Arg Asn Ala Asn Arg Ala Gly Leu Thr Arg
                420                 425                 430
Lys Pro Trp Val Lys Ser Ser Leu Ala Pro Gly Ser Lys Ala Val Gln
                435                 440                 445
Leu Tyr Leu Glu Glu Ala Gly Leu Leu Pro Asp Leu Glu Lys Leu Gly
                450                 455                 460
Phe Gly Ile Val Ala Phe Ala Cys Thr Thr Cys Asn Gly Met Ser Gly
465                 470                 475                 480
Ala Leu Asp Pro Lys Ile Gln Gln Glu Ile Ile Glu Arg Asp Leu Tyr
                485                 490                 495
```

```
Ala Thr Ala Val Leu Ser Gly Asn Arg Asn Phe Asp Gly Arg Ile His
            500                 505                 510
Pro Tyr Ala Lys Gln Ala Phe Leu Ala Ser Pro Leu Val Ile Ala
        515                 520                 525
Tyr Ala Ile Ala Gly Thr Val Arg Phe Asp Ile Glu Lys Asp Ala Leu
            530                 535                 540
Gly Val Asp Ala Ala Gly Lys Pro Val Thr Leu Lys Asp Ile Trp Pro
545                 550                 555                 560
Ser Asp Ala Glu Ile Asp Ala Val Val Thr Ala Ser Val Lys Pro Glu
                565                 570                 575
Gln Phe Arg Lys Val Tyr Glu Pro Met Phe Arg Phe Ala Gln Glu Gln
            580                 585                 590
Thr Gly Lys Ile Asp Pro Leu Tyr Ala Trp Arg Pro Gln Ser Thr Tyr
        595                 600                 605
Ile Arg Arg Pro Pro Tyr Trp Glu Gly Ala Leu Ala Gly Glu Arg Thr
    610                 615                 620
Leu Glu Gly Met Arg Pro Leu Ala Val Leu Gly Asp Asn Ile Thr Thr
625                 630                 635                 640
Asp His Leu Ser Pro Ser Asn Ala Ile Met Ala Asp Ser Ala Ala Gly
                645                 650                 655
Glu Tyr Leu Ala Lys Met Gly Leu Pro Glu Gly Asp Phe Asn Ser Tyr
            660                 665                 670
Ala Thr His Arg Gly Asp His Leu Thr Ala Gln Arg Ala Thr Phe Ala
        675                 680                 685
Asn Pro Lys Leu Ile Asn Glu Met Ala Val Val Asp Gly Gln Val Lys
    690                 695                 700
Gln Gly Ser Leu Ala Arg Leu Glu Pro Glu Gly Lys Val Met Arg Met
705                 710                 715                 720
Trp Glu Thr Ile Glu Thr Tyr Met Asp Arg Lys Gln Pro Leu Ile Ile
                725                 730                 735
Ile Ala Gly Ala Asp Tyr Gly Gln Gly Ser Ser Arg Asp Trp Ala Ala
            740                 745                 750
Lys Gly Val Arg Leu Ala Gly Val Glu Ala Ile Val Ala Glu Gly Phe
        755                 760                 765
Glu Arg Ile His Arg Thr Asn Leu Ile Gly Met Gly Val Leu Pro Leu
    770                 775                 780
Glu Phe Gln Ala Gly Val Asp Arg Lys Thr Leu Gly Ile Asp Gly Thr
785                 790                 795                 800
Glu Thr Phe Asp Val Val Gly Glu Arg Val Pro Arg Ala Thr Leu Thr
                805                 810                 815
Leu Val Ile His Arg Arg Asp Gly Glu Gln Val Gln Val Pro Val Ile
            820                 825                 830
Cys Arg Leu Asp Thr Ala Glu Glu Val Ser Ile Tyr Glu Ala Gly Gly
        835                 840                 845
Val Leu Gln Arg Phe Ala Gln Asp Phe Leu Glu Ser
850                 855                 860

<210> SEQ ID NO 11
<211> LENGTH: 866
<212> TYPE: PRT
<213> ORGANISM: V. cholerae

<400> SEQUENCE: 11

Met Asn Ser Leu Tyr Arg Lys Ala Leu Ser Pro Ser Pro Ala Gln Ser
```

-continued

```
  1               5                   10                  15
Gln Val Asp Phe Phe Asp Thr Arg Ala Val Glu Ala Leu Lys Pro
                20                  25                  30
Gly Ala Tyr Gln Thr Leu Pro Tyr Thr Ala Arg Ile Leu Ala Glu Asn
                35                  40                  45
Leu Val Arg Arg Cys Pro Pro Glu Gln Leu Ser Glu Ser Leu Leu Gln
                50                  55                  60
Ile Ile Glu Arg Lys Arg Asp Leu Asp Phe Pro Trp Tyr Pro Ala Arg
65                      70                  75                  80
Val Val Cys His Asp Ile Leu Gly Gln Thr Ala Leu Val Asp Leu Ala
                85                  90                  95
Gly Leu Arg Asp Ala Ile Ala Glu Gln Gly Gly Asp Pro Ala Gln Val
                100                 105                 110
Asn Pro Val Val Glu Thr Gln Leu Ile Val Asp His Ser Leu Ala Val
                115                 120                 125
Glu Tyr Ser Gly Cys Asp Pro Asp Ala Phe Glu Lys Asn Arg Ala Val
                130                 135                 140
Glu Asp Arg Arg Asn Glu Asp Arg Phe His Phe Ile Glu Trp Cys Lys
145                     150                 155                 160
Thr Ala Phe Lys Asn Val Ser Val Ile Pro Ala Gly Asn Gly Ile Met
                165                 170                 175
His Gln Ile Asn Leu Glu Lys Met Ser Pro Val Ile Gln Val Lys Glu
                180                 185                 190
Gly Val Ala Phe Pro Asp Ser Cys Val Gly Thr Asp Ser His Thr Pro
                195                 200                 205
His Val Asp Ala Leu Gly Val Leu Ala Ile Gly Val Gly Gly Leu Glu
                210                 215                 220
Ala Glu Thr Val Met Leu Gly Arg Pro Ser Met Met Arg Leu Pro Asp
225                     230                 235                 240
Ile Val Gly Val Lys Leu Thr Gly Ala Arg Gln Pro Gly Ile Thr Ala
                245                 250                 255
Thr Asp Ile Val Leu Ala Leu Thr Glu Phe Leu Arg Arg Glu Arg Val
                260                 265                 270
Val Ser Ala Tyr Leu Glu Phe Phe Gly Glu Gly Ala Lys Ala Leu Thr
                275                 280                 285
Ile Gly Asp Arg Ala Thr Ile Ser Asn Met Thr Pro Glu Tyr Gly Ala
                290                 295                 300
Thr Ala Gly Met Phe Tyr Ile Asp Glu Gln Thr Ile Gln Tyr Leu Lys
305                     310                 315                 320
Leu Thr Gly Arg Glu Pro Glu Gln Val Ala Leu Val Glu Ser Tyr Ala
                325                 330                 335
Lys Ala Ala Gly Leu Trp Ala Asp Ser Leu Glu His Ala Glu Tyr Glu
                340                 345                 350
Arg Val Leu Glu Phe Asp Leu Ser Val Glu Arg Asn Leu Ala Gly
                355                 360                 365
Pro Ser Asn Pro His Arg Arg Leu Pro Thr Lys Asp Leu Ser Ala Arg
                370                 375                 380
Gly Ile Ala Ile Pro Ala Gln Gln Arg Glu Ala Gln Gln Ala Glu Gly
385                     390                 395                 400
Leu Met Pro Asp Gly Ala Val Ile Ile Ala Ala Ile Thr Ser Cys Thr
                405                 410                 415
Asn Thr Ser Asn Pro Arg Asn Val Val Ala Ala Gly Leu Leu Ala Lys
                420                 425                 430
```

```
                                -continued

Lys Ala Asn Gln Leu Gly Leu Lys Arg Gln Pro Trp Val Lys Thr Ser
            435                 440                 445

Phe Ala Pro Gly Ser Lys Val Ala Lys Leu Tyr Leu Gln Glu Ala Gly
        450                 455                 460

Leu Leu Ser Glu Leu Glu Gln Leu Gly Phe Gly Ile Val Ala Tyr Ala
465                 470                 475                 480

Cys Thr Thr Cys Asn Gly Met Ser Gly Ala Leu Asp Pro Ala Ile Gln
                485                 490                 495

Gln Glu Ile Ile Glu Arg Asp Leu Tyr Ala Thr Ala Val Leu Ser Gly
            500                 505                 510

Asn Arg Asn Phe Asp Gly Arg Ile His Pro Tyr Ala Lys Gln Ala Phe
        515                 520                 525

Leu Ala Ser Pro Pro Leu Val Ala Tyr Ala Ile Ala Gly Thr Met
        530                 535                 540

Arg Phe Asp Ile Glu Arg Asp Ala Leu Gly His Asp Ala Gln Gly Lys
545                 550                 555                 560

Pro Ile Tyr Leu Asn His Leu Trp Pro Ser Asp Glu Ile Asp Ala
            565                 570                 575

Val Val Gly Arg Ala Val Lys Pro Glu Gln Phe Lys Gln Ile Tyr Ile
            580                 585                 590

Gln Met Phe Lys Leu Asp Glu Thr Gln Ser Ala Ser Ser Pro Leu Tyr
        595                 600                 605

Asp Trp Arg Pro Met Ser Thr Tyr Ile Arg Arg Pro Pro Tyr Trp Glu
        610                 615                 620

Gly Ala Leu Ala Ala Pro Arg Thr Leu Lys Ala Met Arg Pro Leu Ala
625                 630                 635                 640

Ile Leu Gly Asp Asn Ile Thr Thr Asp His Leu Ser Pro Ser Asn Ala
                645                 650                 655

Ile Leu Ala Ser Ser Ala Ala Gly Glu Tyr Leu Thr Lys Met Gly Val
                660                 665                 670

Pro Glu Glu Asp Phe Asn Ser Tyr Ala Thr His Arg Gly Asp His Leu
            675                 680                 685

Thr Ala Gln Arg Ala Thr Phe Ala Asn Pro Lys Leu Phe Asn Glu Met
        690                 695                 700

Val Lys Glu Asn Gly Gln Ile Lys Gln Gly Ser Leu Ala Arg Ile Glu
705                 710                 715                 720

Pro Glu Gly Lys Val Thr Arg Met Trp Glu Ala Ile Glu Thr Tyr Met
                725                 730                 735

Asn Arg Lys Gln Pro Leu Ile Val Ile Ala Gly Ala Asp Tyr Gly Gln
            740                 745                 750

Gly Ser Ser Arg Asp Trp Ala Ala Lys Gly Val Arg Leu Ala Gly Val
        755                 760                 765

Glu Ala Ile Val Ala Glu Gly Phe Glu Arg Ile His Arg Thr Asn Leu
        770                 775                 780

Val Gly Met Gly Val Leu Pro Leu Glu Phe Lys Pro Gly Val Asn Arg
785                 790                 795                 800

His Ser Leu Ala Leu Asp Gly Thr Glu Leu Phe Asp Val Val Gly Glu
                805                 810                 815

Ile Arg Pro Gly Ala Asp Leu Ala Leu Val Val Thr Arg Gln Asn Gly
            820                 825                 830

Glu Lys Leu Asp Val Ala Val Thr Cys Arg Leu Asp Thr Ala Asp Glu
        835                 840                 845
```

-continued

```
Val His Val Tyr Gln Ala Gly Gly Val Leu Gln Arg Phe Ala Gln Asp
    850                 855                 860
Phe Leu
865

<210> SEQ ID NO 12
<211> LENGTH: 860
<212> TYPE: PRT
<213> ORGANISM: S. putrefaciens

<400> SEQUENCE: 12

Met Asn Thr Gln Tyr Arg Lys Pro Leu Pro Gly Thr Ala Leu Asp Tyr
  1               5                  10                  15

Phe Asp Thr Arg Glu Ala Ile Glu Ala Ile Ala Pro Gly Ala Tyr Ala
                 20                  25                  30

Lys Leu Pro Tyr Thr Ser Arg Val Leu Ala Glu Asn Leu Val Arg Arg
             35                  40                  45

Cys Glu Pro Glu Met Leu Thr Ala Ser Leu Lys Gln Ile Ile Glu Ser
 50                  55                  60

Lys Gln Glu Leu Asp Phe Pro Trp Phe Pro Ala Arg Val Val Cys His
 65                  70                  75                  80

Asp Ile Leu Gly Gln Thr Ala Leu Val Asp Leu Ala Gly Leu Arg Asp
                 85                  90                  95

Ala Ile Ala Ala Lys Gly Gly Asp Pro Ala Gln Val Asn Pro Val Val
                100                 105                 110

Pro Thr Gln Leu Ile Val Asp His Ser Leu Ala Val Glu Tyr Gly Gly
            115                 120                 125

Phe Asp Lys Asp Ala Phe Ala Lys Asn Arg Ala Ile Glu Asp Arg Arg
130                 135                 140

Asn Glu Asp Arg Phe His Phe Ile Asn Trp Thr Gln Lys Ala Phe Lys
145                 150                 155                 160

Asn Ile Asp Val Ile Pro Gln Gly Asn Gly Ile Met His Gln Ile Asn
                165                 170                 175

Leu Glu Arg Met Ser Pro Val Ile His Ala Arg Asn Gly Val Ala Phe
            180                 185                 190

Pro Asp Thr Leu Val Gly Thr Asp Ser His Thr Pro His Val Asp Ala
        195                 200                 205

Leu Gly Val Ile Ala Ile Gly Val Gly Gly Leu Glu Ala Glu Ser Val
    210                 215                 220

Met Leu Gly Arg Ala Ser Tyr Met Arg Leu Pro Asp Ile Ile Gly Val
225                 230                 235                 240

Glu Leu Thr Gly Lys Pro Gln Pro Gly Ile Thr Ala Thr Asp Ile Val
                245                 250                 255

Leu Ala Leu Thr Glu Phe Leu Arg Ala Gln Lys Val Val Ser Ser Tyr
            260                 265                 270

Leu Glu Phe Phe Gly Glu Gly Ala Glu Ala Leu Thr Leu Gly Asp Arg
        275                 280                 285

Ala Thr Ile Ser Asn Met Thr Pro Glu Phe Gly Ala Thr Ala Ala Met
    290                 295                 300

Phe Tyr Ile Asp Gln Gln Thr Leu Asp Tyr Leu Thr Leu Thr Gly Arg
305                 310                 315                 320

Glu Ala Glu Gln Val Lys Leu Val Glu Thr Tyr Ala Lys Thr Ala Gly
                325                 330                 335

Leu Trp Ser Asp Asp Leu Lys Gln Ala Val Tyr Pro Arg Thr Leu His
            340                 345                 350
```

```
Phe Asp Leu Ser Ser Val Val Arg Thr Ile Ala Gly Pro Ser Asn Pro
        355                 360                 365

His Ala Arg Val Pro Thr Ser Glu Leu Ala Ala Arg Gly Ile Ser Gly
        370                 375                 380

Glu Val Glu Asn Glu Pro Gly Leu Met Pro Asp Gly Ala Val Ile Ile
385                 390                 395                 400

Ala Ala Ile Thr Ser Cys Thr Asn Thr Ser Asn Pro Arg Asn Val Ile
                405                 410                 415

Ala Ala Gly Leu Leu Ala Arg Asn Ala Asn Ala Lys Gly Leu Thr Arg
            420                 425                 430

Lys Pro Trp Val Lys Thr Ser Leu Ala Pro Gly Ser Lys Ala Val Gln
        435                 440                 445

Leu Tyr Leu Glu Glu Ala Asn Leu Leu Pro Glu Leu Glu Ser Leu Gly
        450                 455                 460

Phe Gly Ile Val Gly Phe Ala Cys Thr Thr Cys Asn Gly Met Ser Gly
465                 470                 475                 480

Ala Leu Asp Pro Val Ile Gln Gln Glu Val Ile Asp Arg Asp Leu Tyr
                485                 490                 495

Ala Thr Ala Val Leu Ser Gly Asn Arg Asn Phe Asp Gly Arg Ile His
            500                 505                 510

Pro Tyr Ala Lys Gln Ala Phe Leu Ala Ser Pro Leu Val Val Ala
        515                 520                 525

Tyr Ala Ile Ala Gly Thr Ile Arg Phe Asp Ile Glu Lys Asp Val Leu
        530                 535                 540

Gly Leu Asp Lys Asp Gly Lys Pro Val Arg Leu Ile Asn Ile Trp Pro
545                 550                 555                 560

Ser Asp Ala Glu Ile Asp Ala Val Ile Ala Ala Ser Val Lys Pro Glu
                565                 570                 575

Gln Phe Arg Lys Val Tyr Glu Pro Met Phe Asp Leu Ser Val Asp Tyr
            580                 585                 590

Gly Asp Lys Val Ser Pro Leu Tyr Asp Trp Arg Pro Gln Ser Thr Tyr
        595                 600                 605

Ile Arg Arg Pro Pro Tyr Trp Glu Gly Ala Leu Ala Gly Glu Arg Thr
        610                 615                 620

Leu Lys Gly Met Arg Pro Leu Ala Val Leu Gly Asp Asn Ile Thr Thr
625                 630                 635                 640

Asp His Leu Ser Pro Ser Asn Ala Ile Met Met Asp Ser Ala Ala Gly
                645                 650                 655

Glu Tyr Leu His Lys Met Gly Leu Pro Glu Glu Asp Phe Asn Ser Tyr
            660                 665                 670

Ala Thr His Arg Gly Asp His Leu Thr Ala Gln Arg Ala Thr Phe Ala
        675                 680                 685

Asn Pro Lys Leu Lys Asn Glu Met Ala Ile Val Asp Gly Lys Val Lys
        690                 695                 700

Gln Gly Ser Leu Ala Arg Ile Glu Pro Glu Gly Ile Val Thr Arg Met
705                 710                 715                 720

Trp Glu Ala Ile Glu Thr Tyr Met Asp Arg Lys Gln Pro Leu Ile Ile
                725                 730                 735

Ile Ala Gly Ala Asp Tyr Gly Gln Gly Ser Ser Arg Asp Trp Ala Ala
            740                 745                 750

Lys Gly Val Arg Leu Ala Gly Val Glu Ala Ile Val Ala Glu Gly Phe
        755                 760                 765
```

-continued

```
Glu Arg Ile His Arg Thr Asn Leu Val Gly Met Gly Val Leu Pro Leu
    770             775                 780

Glu Phe Lys Ala Gly Glu Asn Arg Ala Thr Tyr Gly Ile Asp Gly Thr
785             790                 795                 800

Glu Val Phe Asp Val Ile Gly Ser Ile Ala Pro Arg Ala Asp Leu Thr
            805             810                     815

Val Ile Ile Thr Arg Lys Asn Gly Glu Arg Val Glu Val Pro Val Thr
            820             825                 830

Cys Arg Leu Asp Thr Ala Glu Glu Val Ser Ile Tyr Glu Ala Gly Gly
        835             840                 845

Val Leu Gln Arg Phe Ala Gln Asp Phe Leu Glu Ser
850                 855             860
```

ACONITASE

CROSS-REFERENCE TO RELATED APPLICATION

The present application is related to and claims priority to U.S. Patent Application Ser. No. 60/459,885, filed Apr. 1, 2003 now abandoned. The contents of this application is incorporated herein by reference.

TECHNICAL FIELD

The invention relates to methods to control the growth and virulence of mucoid bacteria and to regulate their production of exopolysaccharide biofilms. The invention also is directed to methods to screen for useful antibiotics. Such screening methods employ a novel aconitase whose properties have heretofore been unknown.

BACKGROUND ART

Several species of bacteria are able to secrete exopolysaccharides or alginates that are essential for virulence as the exudate provides a mechanism for adherence and colonization. One particularly important example of such bacteria is *Pseudomonas aeruginosa*, a common soil bacterium which inhabits individuals generally, but is particularly destructive in subjects with cystic fibrosis. Cystic fibrosis is an autosomal recessive genetic disorder linked to dysfunctional CFTR chloride channels on cell surfaces. It is characterized by production of thick mucus which prevents clearance of bacteria, resulting in chronic infection and inflammation. Because *P. aeruginosa* produces biofilm in the lungs and digestive systems of these subjects, and the subjects are unable to clear this biofilm, *P. aeruginosa* infection is a major cause of death among such individuals.

Many bacteria exhibit mucoid (resembling mucus) phenotype as a response to their growth environment. The mucoidy is generated by bacterial production of extracellular polysaccharides (exopolysaccharide or EPS). Various EPS molecules that include frucose, rugose and glucose residues have been characterized. Examples of bacteria producing mucoid phenotype include alginate producing *Pseudomonas* and *Azotobacter* species (i.e., *P. aeruginosa*, *Azotobacter vinelandii*), rugose producing *Vibrio* species (i.e., *Vibrio cholerae*), xanthan producing *Xanthomonas* species (i.e., *Xanthomonas campestris*), gellan producing *Sphingomonas* species (i.e., *S. paucimobilis*), curdlan-type EPS producing *Cellulomonas*, *Alcaligenes* and *Agrobacterium* species (i.e., *Cellulomonas flavigena*, *Alcalifenes faecalis*) and *Shewanella*, *Bordetella* and *Streptococcus* species producing various uncharacterized EPS, among others. In fact, under unfavorable growth conditions, many bacteria can switch to a mucoid phenotype to resist the environmental stress and adapt to unfavored conditions. Biofilms represent a typical structured adaptation environment in which many bacteria co-exist and secrete extracellular polysaccharides which aid them to stick to surfaces for growth and colonization, provide a protective barrier around them and adapt to their environment in a microbial community. The exopolysaccharides produced by mucoid *Pseudomonas* that occupy the lungs of cystic fibrosis patients are generally alginates which are O-glycosyl linked D-mannuronate and L-guluronate residues.

It is understood that, in order to produce these biofilms, the essential components required must be made available by the metabolic system of the bacterium. The present invention provides means to disrupt this ability by disabling an essential step in this metabolic sequence.

DISCLOSURE OF THE INVENTION

The present inventors have discovered that mucoid bacteria contain an aconitase, designated herein that encoded by acnC which catalyzes the conversion of 2-methyl citrate to 2-methyl isocitrate. This aconitase, which has an activity different from aconitases previously known, is required for the clearance of propionate; propionic acid is a known toxic agent for mucoid bacteria as described in PCT publication WO 01/30997, the disclosure of which is incorporated herein by reference. Accordingly, disruption of the activity or production of acnC protein along with the administration of propionic acid, or of compounds which generate propionic acid, has a deleterious effect on mucoid producing bacteria. This effect resides, in large part, in inhibiting the production of the biofilm and thus inhibiting the ability of the bacterium to survive in its environment.

Thus, in one aspect, the invention is directed to a method to mitigate the virulence of a mucoid bacterial culture or infection, which method comprises contacting the bacteria contained in said culture or infection with an effective amount of propionic acid or a substance which generates propionic acid in combination with effecting inhibition of the production or activity of acnC protein.

In another aspect, the invention is directed to a method to screen for compounds that enhance the toxicity of propionic acid to exopolysaccharide-producing bacteria, which method comprises assessing the ability of candidate compounds to inhibit the activity of acnC protein. This method comprises determining the conversion of 2-methyl citrate to 2-methyl isocitrate in the presence of acnC protein and testing this in the presence and absence of a candidate compound. Compounds whose presence reduces the level of 2-methyl isocitrate produced, or which are otherwise shown to inhibit acnC protein, are identified as useful in enhancing the toxicity of propionic acid or its precursors.

In a third aspect, the invention is directed to a composition of matter which comprises an isolated form of acnC protein, compositions which comprise recombinant materials for its production and methods for producing acnC protein using the recombinant materials. The invention also is directed to antisense or triplex forming nucleic acid molecules and other inhibitors for the production of acnC protein.

BRIEF DESCRIPTION OF THE DRAWINGS

FIGS. 2A–2D show the nucleotide and deduced amino acid sequence of aconitase C from *P. aeruginosa* strain 01 (PA01) as well as homologous enzymes from other bacteria, and position of the encoding gene. In FIG. 2A (SEQ ID NOS:5–6), the nucleotide sequence and deduced amino acid sequence of the acnC protein is shown. FIG. 2B (SEQ ID NO:6) shows the amino acid sequence. In FIG. 2C (SEQ ID NOS:7–12), homologs for the acnC protein having at least 85% similarity were retrieved through BLAST searches and alignment of these sequence using DNASTAR. FIG. 2D shows a comparison of the location of the gene in *P. aeruginosa* and the corresponding genetic positions in *S. typhimurium* and *E. coli*.

MODES OF CARRYING OUT THE INVENTION

While many currently used antibiotics and drugs target the ability of bacteria to grow, they do not necessarily reduce the ability of these bacteria to infect the host, to adapt, and to produce virulence factors. The present invention, by elucidating the function and structure of a protein product and its encoding gene that is involved in virulence and metabolic adaptation, provides an entirely new target for the design and development of new anti-infectives, antibacterial compounds, and biofilm control agents. As this is a new target for antibacterial drugs, resistance to such drugs has not developed.

This target is exemplified herein by the isolation and manipulation of a gene from *Pseudomonas aeruginosa* designated aconitase C (acnC). Disruption of acnC completely abolishes bacterial growth in the presence of propionic acid and results in a significant reduction in the virulence factors associated with *P. aeruginosa*, including the production of biofilms. Hence, inhibition of the production of this protein or inhibition of its activity will attenuate microbial virulence in the presence of propionic acid or a material which generates it. No eukaryotic counterpart to aconitase C is known.

It is demonstrated herein that disruption of aconitase C activity destroys the ability of mucoid bacteria to grow in the presence of propionic acid. Accordingly, it is clear that inhibitors of this activity, either those which inhibit the production of the protein or those which inhibit the activity of the protein itself will be useful in making mucoid bacteria more susceptible to propionic acid and to agents which generate propionic acid.

Figure 1:
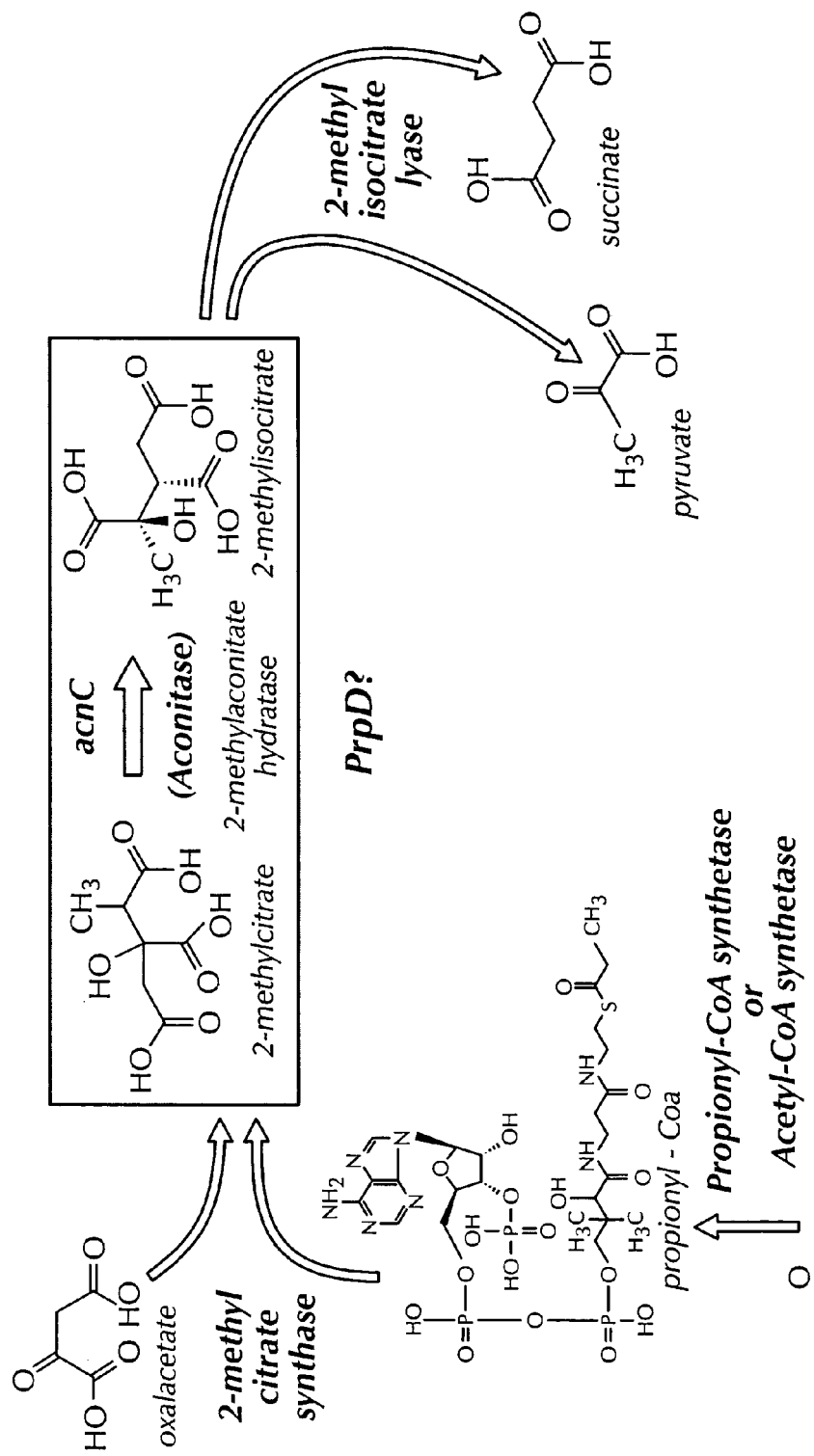
FIG. 1 is a diagram showing the catabolism of propionate in *Pseudomonas aeruginosa*.

Previously described aconitase activities catalyze the dehydration of citric acid to cis aconitate. The presently isolated aconitase C is capable of this activity as well, but has the additional feature of catalyzing the conversion of 2-methyl citrate to 2-methyl isocitrate as shown in FIG. 1. This pathway is critical to propionate metabolism as shown. Propionic acid is converted to propionyl CoA and condensed with oxalacetate to obtain 2-methyl citrate. 2-Methyl citrate must be isomerized to 2-methyl isocitrate in order to complete the metabolic fate of propionic acid. 2-Methyl citrate is metabolized to succinate and pyruvate, components of the citric acid pathway. Inhibition of aconitase C thus diminishes the ability of the organism to metabolize the toxic propionic acid.

"Aconitase C" and "acnC" are used interchangeably and refer to any nucleotide sequence encoding the protein with enzymatic activity, the protein itself, and the gene locus which results in the production of the protein. In order to be defined as "aconitase C" or "acnC" the protein must exhibit the ability to convert 2-methyl citrate to 2-methyl isocitrate. This activity can readily be verified using routine enzymatic assays. In some drawings and text herein, the corresponding materials are also labeled "acaB." In *Pseudomonas*, the acnC encoding gene is found downstream in the propionate operon from prpC and upstream of prpD.

One assay is analogous to that employed for determining levels of aconitase activity known in the prior art, based on the sequence of reactions shown below:

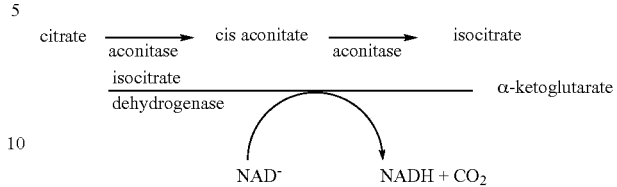

The enzymatic process shown above is monitored spectrophotometrically based on measurement of increase in OD at 340 nm with formation of NADPH from $NADP^+$. The assay components include citrate and isocitrate dehydrogenase. Under appropriate conditions, the rate of NADPH production is proportional to aconitase activity. One aconitase unit will convert 1.0 micromol of citrate to isocitrate per minute at 25° C., pH 7.4 (Gardner and Fridovisch, *J. Chem.* (1992) 267:8757–8763).

As the aconitase C of the present invention converts 2-methyl citrate to 2-methyl isocitrate, and as 2-methyl isocitrate is also oxidized with $NADP^+$ in the presence of isocitrate dehydrogenase, a similar assay that couples spectrophotometric measurement of NADPH production at 340 nm can be used to determine levels of aconitase C of the present invention.

The foregoing, and any other appropriate assay for the conversion of 2-methyl citrate to 2-methyl isocitrate, can be used as a screening assay to identify compounds that will be useful in modifying the virulence of mucoid bacteria. Compounds which inhibit this activity will be useful in this regard. Thus, the activity of a preparation of purified and isolated aconitase C protein, recombinantly produced aconitase C protein, or even an impure preparation of aconitase C protein is tested for this conversion activity in both the presence and absence of candidate compound. Compounds whose presence results in a decrease in this activity are identified as useful compounds for reducing the virulence of mucoid bacteria. As a preliminary screen, the traditional aconitase activity assay shown above can be used as a surrogate in identifying compounds with the desired activity. However, assays using the aconitase C protein per se are preferred.

Figure 2D:
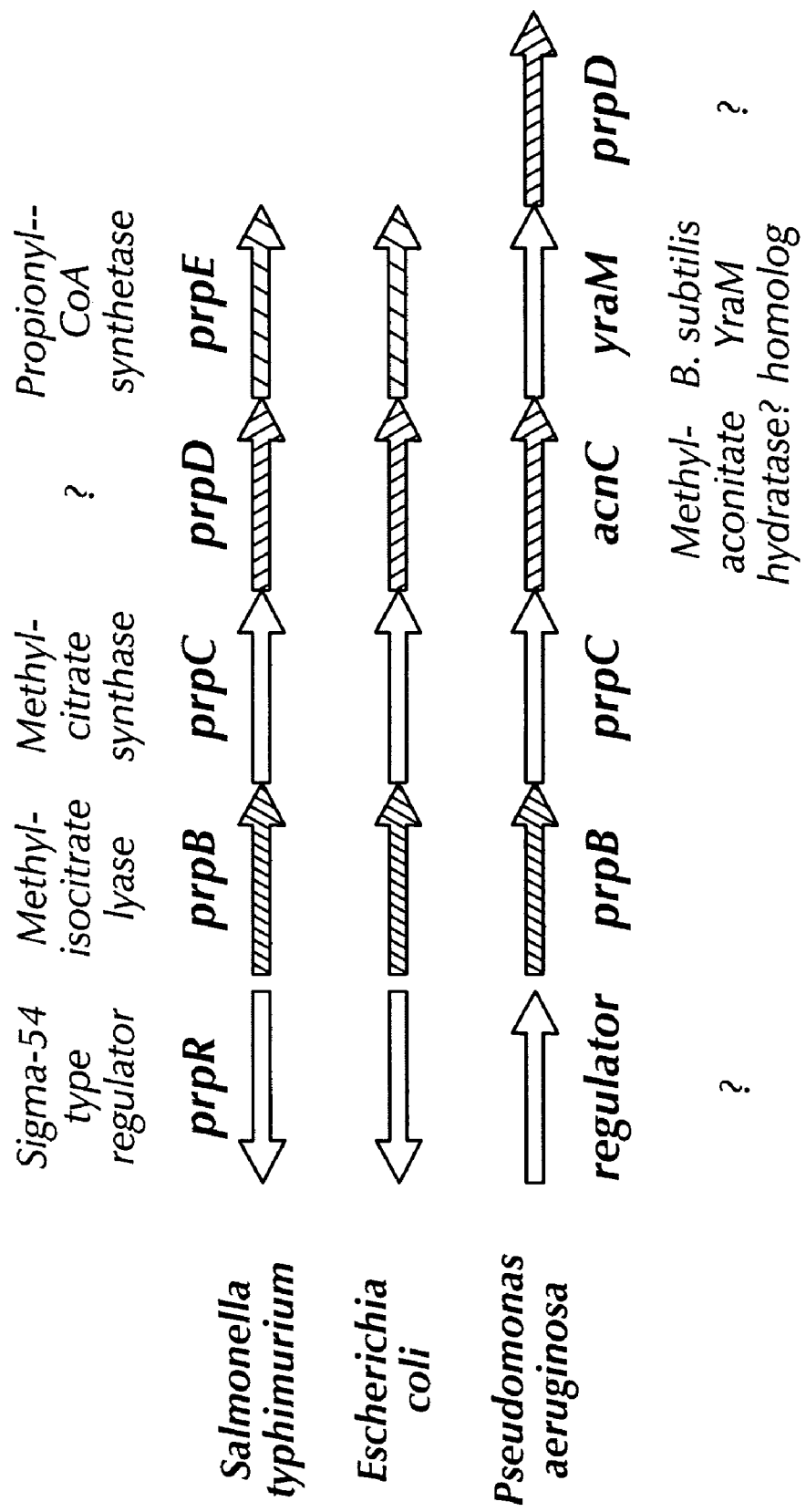

The screening assay using aconitase C protein per se is facilitated by virtue of the availability of recombinant materials for production of the required aconitase C protein. Described herein, as illustrative, is the amino acid sequence of the aconitase C gene derived from *P. aeruginosa*. Homologous proteins from other prokaryotic organisms could also be used, and can readily be retrieved using standard techniques with the information contained in the *P. aeruginosa* gene as a guide. Thus, the protein encoded by the gene in the *P. aeruginosa* strain 01 comprises 869 amino acids and the nucleotide sequence and deduced amino acid sequence are shown in FIG. 2A. The protein is found in the cytoplasm and is probably present in association with bacterial membrane and/or other enzymes involved in propionate catabolism. The aconitase activity in PA acnC::Gm mutant is decreased when measured by a traditional aconitase assay indicating that the catalytic site of the protein may resemble the catalytic site of the known aconitases (acnA and acnB) involving conserved cysteine and arginine residues folded to structure a docking region for an iron-sulfur (4Fe-4S) cubane cluster as well as interaction with substrates including citrate and isocitrate.

Proteins with homology to the PA01 aconitase C protein also share the ability to convert 2-methyl citrate to 2-methyl isocitrate. Thus, included within the scope of the invention are proteins which exhibit at least 85%, preferably 90%, preferably 95%, and more preferably 98% homology over the entire sequence to the sequence shown in FIG. 2A and which exhibit aconitase C activity. "Aconitase C activity" is defined herein as the ability to convert 2-methyl citrate to 2-methyl isocitrate. Fragments of these sequences of shared homology which retain aconitase C activity are also included within the scope of the invention. FIG. 2B shows homologous sequences that are known to occur in other bacteria as retrieved through BLAST searches.

Similarly, proteins encoded by a nucleotide sequence which hybridizes under stringent conditions to a nucleotide sequence encoding the amino acid sequence of the PA01 aconitase C protein are also included within the scope of the invention. The stringency of hybridization is defined by the wash conditions subsequent to the hybridization itself and "stringent" conditions are defined as washing in 0.1% SSC at 65° C.

Thus, proteins which are within the scope of the present invention may be defined in terms of their ability to convert 2-methyl citrate to 2-methyl isocitrate in combination (1) with specified homology to the acnC sequence set forth in FIG. 2A or (2) with structural characteristics as defined by the ability of a nucleotide sequence encoding them to hybridize to a nucleotide sequence encoding this amino acid sequence.

While nucleic acids which encode aconitase C proteins can be defined in terms of nucleotide sequences degenerate with that set forth in FIG. 2A as encoding acnC, nucleic acids comprising nucleotide sequences useful in the design of probes or PCR primers for recovery of acnC proteins from strains of bacteria other than PA01 and for the design of nucleic acids used to inhibit or modulate the production of native acnC will be defined structurally in terms of their homology to the non degenerate nucleotide sequence set forth as encoding acnC in FIG. 2A. Thus, such nucleotide sequences will have at least 85% homology, preferably 90% homology, preferably 95% homology, and more preferably 98% homology to the nucleotide sequence set forth as encoding acnC in FIG. 2A or alternatively in terms of their ability to hybridize to this nucleotide sequence or its complement—i.e., which hybridize under stringent conditions to these sequences.

As stated above, one approach to modulating the virulence of mucoid bacteria comprises contacting such bacteria with a compound which inhibits the aconitase C activity in combination with a source of propionate. Such compounds can be identified through the screening assay described above, or may already be known to block aconitase C activity by virtue of their ability to bind the aconitase C protein. Thus, antibodies or other specific binding partners for the aconitase C proteins of the invention may be employed. "Antibodies" include, in addition to immunoglobulins in general, immunoreactive portions, such as the F(ab) or F(ab') or F(ab')$_2$ fragments; antibodies may also be prepared as single-chain forms—i.e., scFv antibodies. Various ways to manipulate antibodies for particular purposes are also well known; thus, included within the invention are humanized forms of antibodies of the invention or antibodies which are modified to correspond to the species to which they may be administered. Other specific binding partners include aptamers—i.e., nucleic acids which optionally have been selected through known rounds of selection, for example, for specific binding to proteins with aconitase C activity. Such aptamers may be "traditional" nucleic acids or modified forms thereof, such as peptide nucleic acids. Thus, aconitase C activity may be inhibited in a variety of ways, including direct binding of the protein by antibodies or aptamers, and by compounds which have been shown to inhibit the activity empirically.

In addition to use of compounds which inhibit aconitase C activity, methods to inhibit the production of the aconitase C protein itself may also be employed. Such known methods include use of antisense constructs and formation of a triple helix at a critical position in the gene. In these methods, of course, the native, non-degenerate nucleotide sequence must be targeted. Thus, suitable targets for triplex formation or antisense inhibition include nucleotide sequences which encode aconitase C activity and which have at least 85%, preferably 90% homology, preferably 95% homology and more preferably 98% homology to the nucleotide sequence shown to encode acnC in FIG. 2 or nucleotide sequences which hybridize under stringent conditions as defined above to that nucleotide sequence. Typically, oligonucleotides which operate through a mechanism of antisense complementarity are generated in situ. Thus, vectors containing transcriptional controls may be used to generate antisense RNA comprising nucleotide sequences complementary to the mRNA encoding aconitase C (the structural characteristics of which are described above). As triplex formation operates at the gene level, the oligonucleotides for triplex formation are generally directly supplied.

In the method of the invention, the mucoid bacteria for which virulence is sought to be modulated is treated both with materials which inhibit production or activity of aconitase C and with a source of propionate. The propionate source may be propionic acid itself or a fatty acid with an odd number of carbon atoms in the chain which generates propionic acid metabolically. Other materials known to be metabolized to propionic acid, such as ibuprofen, could also be substituted. Thus, the propionic acid portion of the treatment is contributed by any compound which is itself propionic acid or generates propionic acid in situ.

The propionic acid source and the means for modulating aconitase C activity (which means include direct inhibition of activity and inhibition of production of this protein) are supplied either simultaneously or sequentially to the mucoid bacterium target. If the targeted bacterium is present in an in vitro environment, e.g., in a foodstuff or other composition to be decontaminated, the propionic acid source and the modulator of acnC activity can be supplied directly to this material. Alternatively, the offending bacterium may have infected an organism, in which case the appropriate materials are supplied to the organism per se. Thus, for example, if the targeted bacterium has infected an animal, such as a mammal or avian host, the mammal or avian host is provided a propionic acid source and a modulator of acnC. Such administration can be by any traditional means and the materials formulated appropriately to their nature. Thus, administration may be by injection, transmucosal, transdermal, topical, local, systemic, oral, or in a variety of paradigms well known to practitioners.

When the combination of a propionic acid generating compound and inhibitor or modular of acnC is used to treat a subject, the choice of propionic acid generating compound is made appropriate to lack of toxicity and ability of the treated subject to metabolize the precursor to the desired product; thus, for example, propionic acid per se would not be used in mammalian subjects. Suitable formulations are also provided as is known in the art for effective routes of administration.

By "treat" bacterial infection is meant any positive change with regard to the health of the subject related to the underlying infection, not necessarily a complete recovery. Thus, reduction of the mucoid production by the bacteria, amelioration of symptoms, slowing the progression of bacterial growth, and the like, are all within the scope of "treating."

The following examples are intended to illustrate but not to limit the invention.

EXAMPLE 1

Isolation of the Aconitase C Gene from *P. aeruginosa*

The genome of *P. aeruginosa* wildtype strain 01, a mucoid producing strain, designated herein PA01 was subjected to PCR to obtain a 900 base pair aconitase C encoding fragment. The forward primer was GTNGGNACNGAYTCN-CAYACN (SEQ ID NO:1) and the backward primer was NCKNCCYTCRAARTTNCKRTT (SEQ ID NO:2). The amplified fragment was sequenced and the amino acid sequence encoded was deduced. The complete nucleotide sequence and deduced amino acid sequence are shown in FIG. 2A.

The position of the aconitase C encoding gene in *P. aeruginosa* is compared to the location of the corresponding encoding sequence in *S. typhimurium* and *E. coli* in FIG. 2C. *E. coli* and *S. typhimurium* catabolize propionate using proteins encoded by the prpBCDE operon (prp operon). These prp operons have been shown to contain a set of genes—prpR, prpB, prpC, prpD and prpE. The prpD gene in these bacteria has been proposed to encode a protein with 2-methylcitrate dehydratase enzyme activity catalyzing the conversion of 2-methylcitrate into 2-methylisocitrate (Horswill and Escalante-Semerena, *Biochemistry* (2001) 40:4703–4713). In *P. aeruginosa*, the prp operon contains a different set of genes, some of which are homologous to the genes in the *E. coli* and *S. typhimurium* prp operons. The *P. aeruginosa* prp operon contains prpR, prpB, acnC, yraM, and prpD. Neither *E. coli* nor *typhimurium* comprise acnC in the prp operon or elsewhere in their genomes. No sequences homologous to acnC gene have been found in any eukaryotic genome.

Deduction of the aconitase C protein sequence, which contains 869 amino acids, permitted comparison using the BLAST similarity search program to known aconitases. The protein showed 61% similarity using this program to *E. coli* aconitase A, 60% similarity to *P. aeruginosa* aconitase A, 61% similarity to human IRP1, 53% similarity to human IRP2, and 41% similarity to pig mitochondrial aconitase.

EXAMPLE 2

Disruption of the Aconitase C Coding Sequence

The approximately 900 base pairs of the aconitase C insert obtained in Example 1 was amplified by PCR from the PA01 genome using the primers GTGGCACCGACAGC-CATAC (SEQ ID NO:3) and GCGCCCGTCGAAGT-TGCGGTT (SEQ ID NO:4). The amplified fragment was ligated into pBluescript-2 (KS+) (Stratagene) which had been cleaved with EcoRV and treated with tack DNA polymerase and dTTP to form intermediate plasmid pBSacnC. An approximately 1 kb DNA that encodes gentamicin resistance ($Gm^R$) was isolated from pUCGm described in Schweizer, H. D., *Biotechniques* (1993) 15:831–834 by digesting with SmaI. This amplified segment was cloned into the StuI site which resides in the acnC coding sequence in pBSanC to generate pBSacnCGm. The approximately 2 kb DNA fragment which contains the acnC sequence which was disrupted with the $Gm^R$ cassette was isolated by treating this plasmid with HindIII and PstI and filled in with Klenow and dNTP's. This fragment was ligated to the SmaI ends of the conjugation plasmid pEX100T (Schweizer, H. D., et al., *Gene* (1995) 158:15–22) to obtain pEXacnCGm.

This plasmid was used to transform *E. coli* S17-1 and recombinant cells containing the plasmid were combined with an approximately equal amount of PA01 cells and plated on LB plates for conjugation. After conjugation, the bacteria were plated on *Pseudomonas* isolation agar plates containing Gm for selection of residue *P. aeruginosa* cells. Mutants for disruption of the acnC gene were further selected on PIA plates containing Gm and 4% sucrose. The successful transformants are designated PA01* or PA01-acaB:Gm.

EXAMPLE 3

Effects of acnC Gene Disruption

The effect of acnC gene disruption on various virulent activities of PA01 were determined.

Exotoxin A production, determined by Western analysis of stationary phase supernatants did not show any change. However, hemolytic activity (tested by zone clearance on blood agar plates); proteolytic activity (tested by zone clearance on milk agar plates); elastase activity (tested by zone clearance on 2XYT-elastin plates); pyoverdin production (tested by pigment production on F agar plates); and pyocyanin production (tested by pigment production of P agar plates) were all diminished substantially.

When tested for growth on various carbon sources, no difference was observed when glucose, glutamate, citrate, isocitrate, succinate, acetate, pyruvate, butyrate, hexonate, or glyoxalate was used as a carbon source. However, although the wildtype could grow well on propionate, pentanate and the combination of glyoxalate and propionate as carbon sources, the acnC disrupted strain did not grow under these conditions.

Figure 3A:
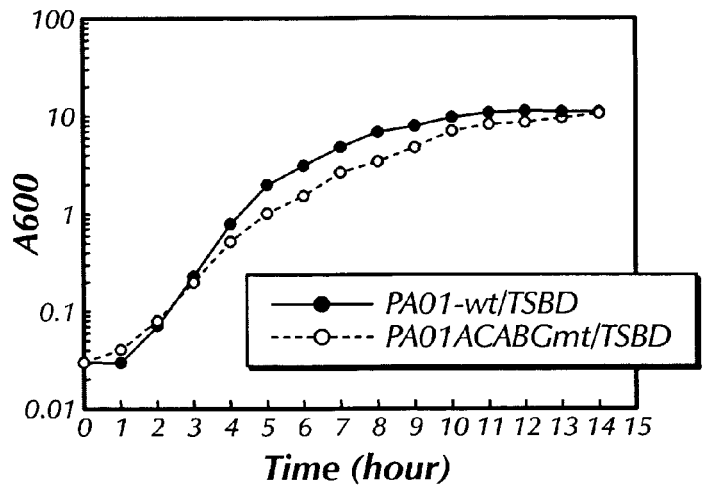
FIG. 3 shows a graph of the effect of 0.5% propionate added to TSBD medium containing 50 mM glutamate on wildtype PA01 as compared to PA01 with an acnC gene disruption.
Figure 3B:
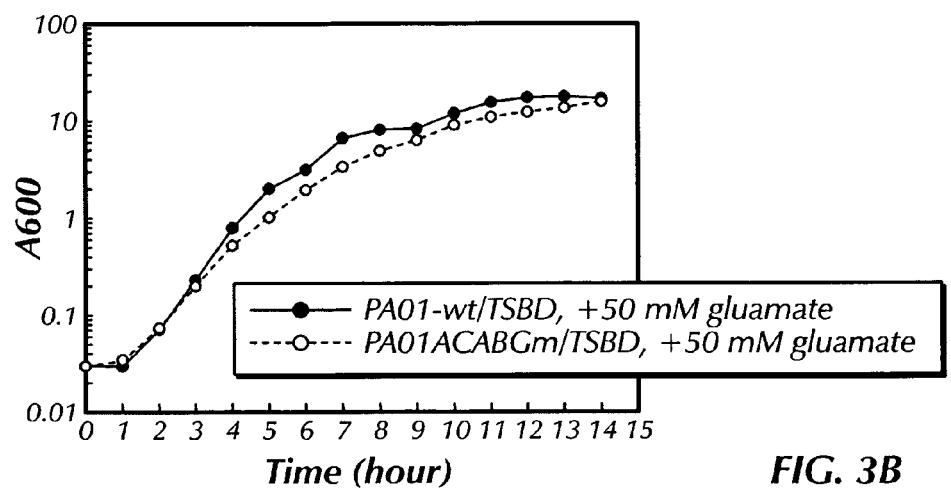
Figure 3C:
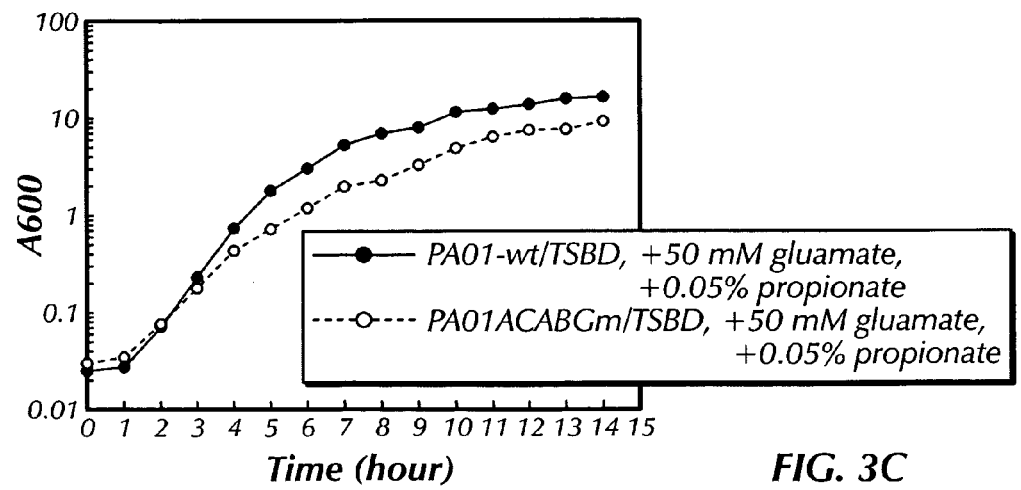

FIG. 3 shows illustrative results of the effect of the inclusion of 0.05% propionate in the tryptic soy broth deferrated (TSBD) plus 100 μM iron medium with and without 50 mM glutamate. As shown, growth is diminished in the presence of propionate in PA01* as compared to wildtype.

The two strains were also tested for aconitase activity using the known conversion of aconitase citric acid to cis aconitic acid. PA01 and PA01* were grown in TSBD supplemented with 100 μM iron and the aconitase activity was determined at 6, 10 and 14 hours. PA01 exhibited 5, 15, and 19 units of activity per milligram of protein at these time points, respectively, while PA01* exhibited only 3, 10, and 16 units, respectively. PA01* also exhibited slightly reduced growth under these conditions.

Thus, disruption of the acnC gene completely abolishes growth in media where propionate is the carbon source, and diminishes growth in propionate-containing media with other carbon sources. Diminished aconitase activity in converting citrate to cis aconitate is also shown.

In addition, it has been shown that chemotaxis is affected and expression of several virulence factors is diminished.

EXAMPLE 4

Studies on Additional Strains

In addition to PA01, an additional mucosal strain, FRD1 with gentamicin resistance was subjected to disruption of the acnC gene, as was a mucoid clinical isolate. For comparison, aconitase A was also similarly disrupted. All of the strains behaved similarly in respect to their ability to grow on propanediol in the presence and absence of propionic acid. All of the strains were able to grow in 1,2-propanediol, but were less able to grow using 1,3-propanediol as carbon source. Addition of propionic acid to the medium completely abolished the ability of both PA01 and FRD1 with disrupted aconitase C genes to grow under these conditions; disruption of the acnA gene did not result in this effect.

FRD1 is much more susceptible to propionate inhibition than wildtype PA01. While PA01 is able to grow on 0.4% propionate, inhibition of FRD1 growth occurs at levels of 0.1% propionate and inhibition is complete as low as 0.2% propionate in the medium.

It has also been noted that aconitase activity (measured as the conversion of citric acid to cis aconitate) is different in PA01 wildtype as compared to FRD1. While this activity was slightly higher in FRD1 after 4 hours of culture as compared to PA01, after 7 hours of culture the activity was statistically higher in PA01 cells and roughly equivalent after 14 hours.

Figure 4:
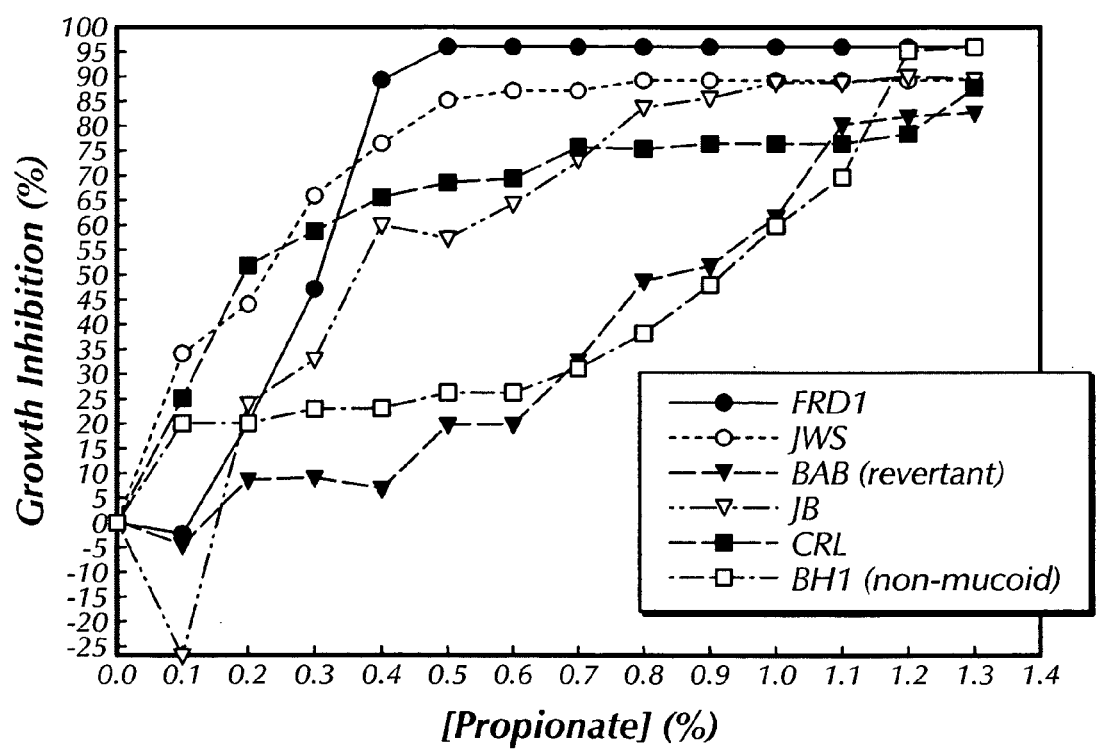
FIG. 4 shows the effect of the addition of propionate to clinical mucoid isolates.

FIG. 4 shows the effect of the addition of propionate on the growth of various mucoid clinical isolates in comparison with a non-mucoid strain, BH1, and a revertant strain, BAB. As shown, the mucoid strains demonstrate substantial growth inhibition at low concentrations of propionate.

It has also been shown that the results of propionate treatment can be obtained using odd-numbered chain fatty acids in the medium, as the metabolic products of these fatty acids include propionate. This is shown in Table 1 below which shows results of the addition of propionate, butyrate, hexanoic acid and pentanoic acid to M9 medium on wild-type PA01*, and PA01 with two irrelevant disruptions—acaA and icdI. As shown, both the presence of 0.4% propionate and 0.4% pentanoate disrupt the growth of the strain with a disrupted acnC gene, but these additions have no effect on the other strains tested.

TABLE 1

|  | PA01 wt | Disrupted acaA | PA01* (Disrupted acnC) | Disrupted IcdI |
|---|---|---|---|---|
| M9/propionate 0.4% | + | + | − | + |
| M9/butyrate 0.4% | +/poor | +/poor | +/poor | +/poor |
| M9/hexanoate 0.4% | + | + | + | + |
| M9/pentanoate 0.4% | + | + | − | + |

The effect of the addition of 0.4% propionate to LB medium containing wildtype PA01, PA01*, and the more sensitive mucoid strain FRD1, was also tested. The wildtype does not respond to 0.4% propionate, but the modified strain PA01* containing a disrupted acnC gene does show diminished growth, as does the more propionate-sensitive strain FRD1.

EXAMPLE 5

Effect of TCA Intermediates

FRD1, as set forth in Example 4, shows enhanced sensitivity to propionate, possibly due to reduced levels of TCA cycle activity, since propionic acid drains the TCA cycle intermediate oxalacetic acid.

This effect was tested by supplementing M9 minimal media with various TCA cycle components in the presence of 0.4% propionate. While glucose as a carbon source failed to reverse the negative effects on growth of propionate, the cell cycle intermediates acetate, aspartate, glutamate and malate were successful in doing so.

EXAMPLE 6

Effect of Ibuprofen on Growth of FRD1

Ibuprofen is known to generate propionic acid when metabolized and was thus tested for its ability to inhibit the growth of FRD1. Other propionate-generating compounds include certain $\alpha_4\beta_1$ integrin antagonists described by DuPlantier, A. J., et al., Bioorg. Med. Chem. Let. (2001) 11:2593–2596. Using absorbance at 600 nm as the criterion, growth inhibition was detected at a concentration of 0.5 mg/ml of ibuprofen added to 2 ml LB cultures; the percent inhibition at this level was 19%. Inhibition increased in a dose-dependent manner to 72% at 5 mg/ml, and was similar at 10 mg/ml (73%).

EXAMPLE 7

Effect of Propionate on Attachment

As mucoid production is necessary for attachment, the effect on mucoid production of addition of propionate can be tested by assessing the level of attachment of the cells to plastic tubes. This was measured as the absorbance at 570 nm of plastic tubes. Levels of as low as 0.1% propionate were able to diminish significantly the attachment of FRD1 cells to plastic tubes; the effect on attachment of PA01 was less dramatic.

EXAMPLE 8

Effect of Propionate on Antibiotic Susceptibility of PA01 and FRD1

The effect of various concentrations of propionate on the ability of antibiotics to curtail the growth of PA01 or FRD1 was tested. Levels of 0.2% propionate appeared to have no effect on PA01 growth in the presence of the antibiotics amikacin, carbenicillin, ciprofloxacin, tobramycin, and tetracycline. Growth was assured by the diameter of colonies formed in the presence of discs containing amikacin (AN-30), 30 μg, carbenicillin (CB-100), 100 μg, ciprofloxacin (CIP-5), 5 μg, tobramycin (NN-10), 10 μg, or tetracycline (TE-30), 30 μg. On the other hand, 0.2% propionate appeared to diminish the effect of CB-100 and CIP-5 on inhibiting growth of FRD1. There appears to be little, if any, effect on the efficiency of remaining antibiotics tested.

The invention claimed is:

1. An isolated and purified recombinant protein which comprises the amino acid sequence of SEQ ID NO: 6.

2. An isolated and purified recombinant protein which consists of an amino acid sequence which is at least 98% sequence homologous to the amino acid sequence of aconitase SEQ ID NO: 6 over its entire length and which exhibits enzymatic activity to convert 2-methyl citrate to 2-methyl isocitrate.

3. A method to identify a test compound that, in combination with propionic acid, inhibits the virulence of mucoid bacteria, which method comprises assessing the activity of the protein of claim 2 in the presence and absence of a test compound; comparing the activity in the presence and absence of said test compound, wherein a decrease in activity in the presence of said test compound, as compared to its absence, identifies said test compound as able to mitigate virulence of mucoid bacteria in the presence of propionic acid.

4. The method of claim 3, wherein said assessing is by measuring the decrease in concentration of 2-methyl citrate or the increase in concentration of 2-methyl isocitrate.

5. A method to identify a test compound that, in combination with propionic acid, inhibits the virulence of mucoid bacteria, which method comprises assessing the activity of the protein of claim 1 in the presence and absence of a test compound; comparing the activity in the presence and absence of said test compound, wherein a decrease in activity in the presence of said test compound, as compared to its absence, identifies said test compound as able to mitigate virulence of mucoid bacteria in the presence of propionic acid.

* * * * *